(12) United States Patent
Shahinpoor et al.

(10) Patent No.: US 6,475,639 B2
(45) Date of Patent: *Nov. 5, 2002

(54) IONIC POLYMER SENSORS AND ACTUATORS

(75) Inventors: Mohsen Shahinpoor, 9910 Tanoan Dr. N.E., Albuquerque, NM (US) 87111; Mehran Mojarrad, Albuquerque, NM (US)

(73) Assignee: Mohsen Shahinpoor, Albuquerque, NM (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 102 days.

(21) Appl. No.: 09/258,602

(22) Filed: Feb. 26, 1999

(65) Prior Publication Data

US 2002/0039620 A1 Apr. 4, 2002

Related U.S. Application Data

(63) Continuation-in-part of application No. 09/101,856, filed as application No. PCT/US96/17870 on Nov. 6, 1996, now Pat. No. 6,109,852.
(60) Provisional application No. 60/076,302, filed on Feb. 27, 1998, and provisional application No. 60/013,617, filed on Jan. 18, 1996.

(51) Int. Cl.⁷ .............................. B32B 15/08; A61F 2/08
(52) U.S. Cl. ..................... 428/614; 428/621; 428/626; 428/655; 428/670; 623/14.13
(58) Field of Search .............................. 427/2.12, 2.24; 623/14.13; 428/614, 621, 626, 655, 670

(56) References Cited

U.S. PATENT DOCUMENTS

| | | | | |
|---|---|---|---|---|
| 3,989,035 | A | * 11/1976 | Zuehlsdorff | ............... 600/391 |
| 4,083,765 | A | * 4/1978 | Lawson | ............... 204/195 W |
| 4,272,353 | A | 6/1981 | Lawrance | |
| 4,328,086 | A | 5/1982 | Takenaka et al. | |
| 4,364,803 | A | 12/1982 | Nidola et al. | |
| 4,417,959 | A | 11/1983 | Kadija et al. | |
| 4,449,599 | A | 5/1984 | Creek | |
| 4,496,451 | A | 1/1985 | Ishii et al. | |
| 4,522,698 | A | 6/1985 | Maget | |
| 4,537,910 | A | 8/1985 | Oogai et al. | |

(List continued on next page.)

OTHER PUBLICATIONS

Asaka, K., et al., "Bending of Polyelectrolyte Membrane—Platinum Composites by Electric Simulli I. Response characteristics to Various Waveforms," *Polymer Journal*, vol. 27, No. 4, pp 436–440 (1995).

Burroughs, C., "UNM's Muscle Research," *Albuquerque Business Times*, Nov. 11–25, 1996.

(List continued on next page.)

*Primary Examiner*—Shrive P. Beck
*Assistant Examiner*—Kirsten A. Crockford
(74) *Attorney, Agent, or Firm*—Dennis F. Armijo

(57) ABSTRACT

Ion exchange membrane-based sensors, actuators and sensor/actuators and methods of making same for applications requiring sensing, actuating and controlling displacement. Sensors, actuators, and sensor/actuators are useful in biological as well as other applications. Encapsulation of the sensors, actuators, or sensor/actuators further increases the utility of the present invention. Devices according to the present invention made using lithium are preferred over those made using only sodium.

20 Claims, 22 Drawing Sheets

U.S. PATENT DOCUMENTS

| | | | |
|---|---|---|---|
| 4,546,010 A | | 10/1985 | Killer et al. |
| 4,565,487 A | | 1/1986 | Kroczynski |
| 4,578,045 A | | 3/1986 | Mayer |
| 4,681,855 A | * | 7/1987 | Huang .......................... 436/39 |
| 4,717,581 A | * | 1/1988 | Robblee .................... 427/2.12 |
| 4,748,737 A | | 6/1988 | Charles et al. |
| 4,818,353 A | | 4/1989 | Langer et al. |
| 4,835,395 A | * | 5/1989 | McManus et al. .......... 250/435 |
| 4,858,063 A | * | 8/1989 | Laue et al. ................. 361/286 |
| 4,919,891 A | * | 4/1990 | Yafuso et al. .............. 427/2.12 |
| 4,940,318 A | | 7/1990 | Ealey et al. |
| 4,959,132 A | | 9/1990 | Fedkiw, Jr. |
| 5,038,821 A | | 8/1991 | Maget |
| 5,062,841 A | | 11/1991 | Siegel |
| 5,098,659 A | * | 3/1992 | Yim et al. ................. 427/2.12 |
| 5,100,933 A | | 3/1992 | Tanaka et al. |
| 5,190,813 A | | 3/1993 | Ohashi et al. |
| 5,250,167 A | | 10/1993 | Adolf et al. |
| 5,268,082 A | | 12/1993 | Oguru et al. |
| 5,275,820 A | * | 1/1994 | Chang ....................... 427/2.12 |
| 5,279,559 A | | 1/1994 | Barr |
| 5,334,304 A | * | 8/1994 | Maget ........................ 204/421 |
| 5,389,222 A | | 2/1995 | Shahinpoor |
| 5,471,185 A | | 11/1995 | Shea et al. |
| 5,481,152 A | | 1/1996 | Buschulte |
| 5,529,279 A | | 6/1996 | Beatty |
| 5,531,664 A | | 7/1996 | Adachi et al. |
| 5,531,878 A | * | 7/1996 | Vadgama et al. ........... 204/403 |
| 5,554,272 A | * | 9/1996 | Benco et al. ............ 205/782.5 |
| 5,556,700 A | | 9/1996 | Kaneto et al. |
| 5,614,246 A | * | 3/1997 | Mund et al. ............... 427/2.24 |
| 5,685,837 A | * | 11/1997 | Horstmann ................ 427/2.12 |

OTHER PUBLICATIONS

Millet, P., et al., "Preparation of Solid Polymer Electrolyte Composites: Investigation of the Ion–Exchange Process," *Journal of Applied Electrochemistry*, vol. 25, pp 227–232 (1995).

Millet, P., et al., "Preparation of Solid Polymer Electrolyte Composites: Investigation of the Ion–Exchange Process," *Journal of Applied Electrochemistry*, vol. 25, pp 233–239 (1995).

Millet, P., et al., "New Solid Polymer Electrolyte Composites for Water Electrolysis," *Journal of Applied Electrochemistry*, vol. 19, pp 162–166 (1989).

Millet, P., et al., "Preparation of New Solid Polymer Electrolyte Composites for Water Electrolysis," *Int. J. Hydrogen Energy*, vol. 15, No. 4, pp 245–253 (1990).

Mojarrad, M., et al., "Ion–Exchange–Metal Composite Sensor Films," *SPIE*, vol. 3042 (1997).

Oguro, K., et al., "Polymer Film Actuator Driven by a Low Voltage," $4^{th}$ *Int'l Symp on Micro and Human Science*, Jagiya, Japan (1993) pp 39–40.

Sadeghipour, et al., "Development of a Novel Electrochemically Active Membrane and 'Smart' Material Based Vibration Sensor/Damper," *Smart Materials Struc*, vol. 1, pp 172–179 (1992).

Furlow, B., "(Muscle) Bound for Glory", *Mirage–University of New Mexico*, Spring 1997.

Shahinpoor, M., "The Ionic Flexogelectric Effect in Polymeric Gels" *School of Engineering UNM* (1996).

* cited by examiner

US 6,475,639 B2

IONIC POLYMER SENSORS AND ACTUATORS

CROSS-REFERENCE TO RELATED APPLICATIONS

This application is a continuation-in-part of U.S. patent application Ser. No. 09/101,856, filed Feb. 5, 1999, now U.S. Pat. No. 6,109,852, which is the U.S. national stage of Patent Cooperation Treaty Application Serial No. PCT/US96/17870, filed Nov. 6, 1996, and claims the benefit of U.S. Provisional Patent Application Serial No. 60/013,617, filed Jan. 18, 1996. This application also claims the benefit of the filing of Provisional Application Serial No. 60/076,302, entitled "Ionic Polymer Sensors," filed on Feb. 27, 1998.

BACKGROUND OF THE INVENTION

1. Field of the Invention

The present invention relates to a novel method of manufacturing actuators, sensors and novel applications of the actuators and sensors manufactured according to the novel method.

2. Background Art

The creation of sensors and controllable actuators, or synthetic muscles, is known. Sensors and artificial muscles or actuators made from ion-exchange membranes are relatively new but also known.

U.S. Pat. No. 4,364,803, to Nidola et al., discloses a process for deposition of catalytic electrodes on ion-exchange membranes and an electrolytic cell made by the process. The process involves contacting a water-swollen, roughened membrane with an amphoteric organic or metal salt thereof, such as alkali metal salts thereof, e.g., platinum, palladium, and nickel. After further processing, the membrane is then contacted with a solution of the selected metal salt wherein sorption of the metal salts takes place mainly on the membrane surface in the vicinity of the polar groups of the polymer or the pre-adsorbed polar groups of the amphoteric organic. The absorbed/adsorbed metal creates the catalytic electrodes. The patent discloses operation of the electrode in the presence of sodium brine/caustic soda.

U.S. Pat. No. 4,522,698, to Maget, discloses a prime mover that uses pressure increases and decreases induced by converting molecules of electrochemically active material to ions, transporting ions through an electrolytic membrane and reconverting the ions to molecules. The prime mover includes gas-tight compartments filled with an electrochemically active material and separated by an electrolytic membrane, such as an ion-exchange membrane, that incorporates electrodes so that a voltage gradient can be established across the membrane to induce current flow through the membrane. When the current flows through the membrane, molecules travel through the membrane and are reconverted to molecules in the opposite compartment causing a pressure increase in the receiving compartment and a pressure decrease in the other compartment. The pressure changes are converted to mechanical motion that can be used as a driver for a mechanical load. The disadvantages of this technique are that the resulting motion is small and the pressure increase may rupture the membrane.

U.S. Pat. No. 4,748,737, to Charles et al., discloses a method of removing surface oxidation from particulates. The method includes removing oxide film from particulates with a liquid reducing agent or strong acid comprising an alkali metal., or a hydroxide of an alkali metal, wherein alkali metals such as sodium, lithium, potassium, or mixtures thereof are used.

U.S. Pat. No. 5,100,933, to Tanaka, et al., discloses the use of ionized cross-linked polyacrylamide gels as engines or artificial muscles; the gels can contain a metal ion and are capable of discontinuous volume changes induced by infinitesimal changes in environment. The gel is made by dissolving acrylamide monomers and bisacrylamide monomers in water, adding a polymerization initiator (in particular, ammonium persulfate and TEMED, or tetramethyl-ethylene-diamine) to the solution, soaking the gel sample in water to wash away all residual monomers and initiators, immersing the gel in a basic solution of TEMED for up to 60 days, then immersing the gel in a solvent (in particular, acetone, acetone in water, ethanol and water, or methanol and water). The primary disadvantages of these actuators are generally that the response time of the gel is much longer than that of other known actuator components and that the gel must be contained in the solvent bath. The gels are also mechanically brittle and easily broken.

U.S. Pat. No. 5,250,167, to Adolf, et al., discloses actuators or synthetic muscles, using polymeric gels contained in compliant containers with their solvents; these actuators undergo substantial expansion and contraction when subjected to changing environments. The actuators may be rigid or flexible and may be computer-controlled. The driver may also be electrolytic, where application of a voltage across the polymer gel causes a pH gradient to evolve between the electrodes. For example, filling the polymer fibers with platinum by alternatively treating them with solutions of platinic chloride and sodium borohydride obtains a reversible expansion and contraction of the fiber with the application of an electric field. The actuating gel itself is the only moving part required and the electric field may be only on the order of a few volts per centimeter. The disadvantage is that actuator performance is dictated by the parameters of the polymeric gel used. Furthermore, liquid containment is required to make the actuators stronger and not so easily broken.

U.S. Pat. No. 5,268,082, to Oguro et al., discloses an actuator element based on a membrane electrode that when subject to a DC voltage of 0.1 Volts to 2.0 Volts undergoes a displacement proportional to the square of its length (Col. 3; II. 4, 5). This description of the displacement in relation to membrane electrode length is patently erroneous. For example, for a length of unity, the displacement would be also unity. Consider further, for a length less than unity, the displacement would be greater than the length whereas for a length of 100, displacement would be less than the length, i.e., 10% of the length. Therefore, the specification relating to displacement is in error. Even if the specification were to have meant square "root," ambiguity and vagueness would remain. Further ambiguities exist in the specification of this patent. For instance, in Example 4 (Col. 5; I. 27), a clamped membrane having a length of 5 mm extending beyond the clamp was placed in a salt water solution and exposed to a rectangular wave on the order of 0.1 Hz. For this example, a tip displacement of 10 mm was measured. This is a physical impossibility. In Example 5, an actuator element as used in Example 4 produced a displacement of +/−0.36 mm (Col. 6; II. 18–20). The specification states that this displacement was about 1.8 times that of Example 4 (Col 6; II. 18–22), or approximately 18 mm. All of the foregoing descriptions related to membrane tip displacement are obviously in error. However, in another example, Example 3, a membrane 3 mm in length was placed in a 4% salt-water solution and exposed to 1.6 Volts resulting in a tip displacement of 0.3 mm, 10% of length. Therefore, one of ordinary skill in the art would conclude that the specification does not enable nor support tip displacements greater than 10% of the membrane length.

U.S. Pat. No. 5,389,222, to Shahinpoor, discloses electrically controllable polymeric gel actuators or synthetic muscles, using gels made of polyvinyl alcohol, polyacrylic acid, polyacrylonitrile, or polyacrylamide contained in an electrolytic solvent bath. These actuators operate by reacting to changes in the ionization of a surrounding electrolyte by expanding or contracting, and can be spring-loaded and/or mechanically biased for specific applications. Polymeric gel configurations such as sheets, solid shapes or fiber aggregates are contemplated, as are the use of a salt water solution for the electrolyte, and a platinum catalyst in the actuator housing to recombine the hydrogen and oxygen produced as a result of electrolysis during ionization of the electrolyte. Again, liquid containment is required to maintain strength and electric controllability, and not enough deformation or displacement is generated.

U.S. Pat. No. 5,531,664, to Adachi et al., discloses a bending actuator having a coil sheath with a fixed distal end and a free proximal end. The distal end portion of the device is formed of an axially expanding and contracting shape memory alloy. The device produces adequate drive force to bend the bendable portions of medical probes incorporating the actuator. The ability to bend such probes facilitates in situ navigation.

"Development of a Novel Electrochemically Active Membrane and 'Smart' Material Based Vibration Sensor/Damper," by Sadeghipour et al., *Smart Materials and Structures*, Vol. 1, pp. 172–179, (1992), discloses "smart" materials developed from metalized NAFION® (E.I. du Pont de Nemours and Company) membranes that may be used for vibration sensing and damping applications. For sensing applications, the smart NAFION®-based viscoelastic material generates a voltage response when subject to mechanical vibrations. For damping applications, the material dissipates mechanical or pressure induced voltage potentials (electrical energy) as heat energy. The article also discloses a method of making the smart materials comprising steps of platinum deposition onto a NAFION® membrane and saturation of the platinum coated metal with hydrogen under high pressure, or alternatively, exposing the platinum coated membrane to dissolved hydrogen. Applications for the smart material include: integration into cantilever structures, such as robot arms, aircraft wings, etc., for damping; use as a vibration cell accelerometer; and use as a pressure cell. For vibration cell sensors, the authors reported voltage response over the frequency range of approximately 100 Hz to approximately 3000 Hz. Load response was also reported at 500 Hz and 1000 Hz. A plot of simulated tip deflection versus time for an electrically damped metal-NAFION® composite beam were reported for initial positive tip deflections of 1% of beam length. Because no beam lengths were given, the magnitude of displacement cannot be determined. All smart materials disclosed in this article rely on hydrogen as a cation.

Thus, there is an existing need for soft sensors and actuators that allow for a high degree of bending, i.e., displacement. Further, a need exists for such sensors and actuators to perform sensing and activation noiselessly and efficiently (as do biological muscles). Actuators with a low ratio of mass to power or a high ratio of power or force to mass are also in need, as are sensors with a high output signal strength in relation to sensory input.

SUMMARY OF THE INVENTION (DISCLOSURE OF THE INVENTION)

In view of the above-described needs, it is a primary object of this invention to provide actuators and sensors for actuating and/or sensing displacement, rotation, force, torque, acceleration, frequency, concentration, charge, and degradation. In particular, a primary object of this invention is to provide actuators, sensors and actuators/sensors that are capable of undergoing unprecedented displacement.

In a preferred embodiment, the present invention comprises a sensing device comprising an ion exchange, lithium-treated membrane and a metallic coating on the membrane forming at least one electrode wherein bending of the membrane generates electrical potential between at least one electrode and another point. Lithium treatment during making of membrane-based sensors and/or actuators enhances overall sensitivity of sensors and activity of actuators in comparison to, for instance, sodium treatment. Lithium treatment includes, but is not limited to, use of LiOH, $LiBH_4$, and mixtures of lithium and other cations. Sensing devices according to this embodiment comprise at least one electrode wherein incorporation of many electrodes is possible. However, the device is not limited to electrodes solely on the membrane because a point removed from the device can serve as an electrode, including a point within an electrically conductive solution.

In another preferred embodiment, the present invention comprises a sensing device comprising an ion exchange membrane having a length defining a relative path wherein the membrane comprises at least two parts fixed to positions along the path and a metallic coating on the membrane. The metallic coating forms at least one electrode wherein bending of the membrane displaces at least one part of the membrane, at a position between at least two fixed positions, thereby generating an electrical potential between the at least one electrode and another point. Sensor devices according to this embodiment serve to sense phenomena not only at end points of the sensor device but also at a point interior to the end points. For instance, such embodiments can sense wave phenomena that cause local or global displacement of the membrane-based sensing device. For this particular embodiment, the relative path need not be defined along a major length because membrane-based sensors of the present invention can take a variety of shapes, some having multiple lengths. The ability to sense along multiply defined lengths defining multiple paths is also a feature of the present invention. To accomplish sensing along multiple lengths, or even along a single length, the ability to incorporate multiple electrodes exists.

In yet another preferred embodiment, the present invention comprises a sensing device comprising an ion exchange membrane having a length defining a relative path wherein the membrane comprises at least one part fixed to a position along the path and a metallic coating on the membrane forming at least one electrode wherein bending of the membrane to displace at least one part of the membrane from the path by at least 1% of the length generates an electrical potential between the at least one electrode and another point. In this embodiment, the path defined by a length of the membrane-based sensor is relative because the sensor can move in space. For instance, for a sensor implanted in a body, movement of the body can alter the global position of the sensor, however, local displacement of the sensor with respect to the sensor itself generates a measurable signal. Another preferred embodiment of the present invention comprises a sensing device as described, however, bending of the membrane to displace at least one part of the membrane from the path by at least 0.1 mm generates an electrical potential between the at least one electrode and another point. Overall, some embodiments of the present invention rely on a scaler value displacement measured in length and some rely on a relative scaler value displacement measured in terms of percentage of a membrane sensor length.

Membrane-based sensors of the present invention comprise material properties. In a preferred embodiment of the present invention, an ion exchange membrane for use in a membrane-based sensor device has a material property selected from the group consisting of mechanical, rheological, chemical, thermal, magnetic, and electrical. Of course, such a device also has a metallic coating on the membrane wherein the metallic coating forms at least one electrode wherein application of an electrical potential between the at least one electrode and another point alters the material property.

A further preferred embodiment of the present invention comprises a sensing device comprising an ion exchange membrane and a metallic coating on the membrane wherein the metallic coating forms at least one electrode wherein displacement of the membrane generates a measurable signal useable in a feedback control system. In such a device the feedback control signal can feed back to the sensor device, for instance, to maintain the sensor in a predetermined position.

In another preferred embodiment, the present invention comprises a sensing and actuating device comprising an ion exchange membrane and a metallic coating on the membrane forming at least one electrode. Such a sensing and actuating device can comprise a feedback control system.

Several preferred embodiments of the present invention comprise a sensing or actuating device comprising an ion exchange membrane, a metallic coating on said membrane forming at least one electrode, and a surrounding coating forming an outer surface of the sensor or actuator device. The presence of a surrounding coating is advantageous for several reasons. For instance, the surrounding coating can encapsulate the membrane device. The surrounding coating can also provide for biocompatibility with biological material in which the sensing device is placed. Furthermore, a surrounding coating can effectively protect a pharmacological material that is in proximity with the sensing device. A surrounding coating of these embodiments of the present invention can permit transport of at least one member selected from the group consisting of mass transport and energy transport. In addition, a surrounding coating can comprise a non-porous material.

Combinations and variations of the aforementioned embodiments are useful and describe herewithin. For instance, a sensor/actuator membrane-based device with a permeable coating can function as a drug delivery system. By mechanical, electrical, and/or chemical means, the sensor can generate and transmit a signal to actuate a mechanism to induce drug delivery. Ideally for some applications, such a system is programmable to achieve zero order drug delivery, i.e., where the drug concentration within the body does not vary over time. When appropriately placed, devices according to the present invention, can stimulate natural processes within the body through a variety of means, including mechanical, electrical and chemical simulation.

The methods for making actuators, describe below, also applies for making sensor and sensor/actuators. The limitations associated with existing actuators and the methods for their manufacture are overcome by the present invention which provides a method of preparing actuators (synthetic muscles) comprising the steps of: rinsing an ion-exchange material; coating the ion-exchange material with a substance which undergoes chemical reduction in the presence of a reducing agent; and reducing the coating on the ion-exchange material by exposing the ion-exchange material to a reducing agent. In the preferred embodiment, the ion-exchange material comprises a material selected from the group consisting of ion-exchange membranes, ionomer membranes, ion-exchange resins, gels, beads, powders, filaments, and fibers, preferably an ion-exchange membrane, more preferably a polymer ion-exchange membrane, and most preferably a perfluorinated sulfonic acid ion-exchange polymer membrane. Rinsing is best performed in water. The ion-exchange material preferably has at least two surfaces and rinsing is preceded by roughening the surfaces of the ion-exchange material, such as by sandblasting with fine glass bead sandblast. Rinsing is also preferably preceded by cleaning the ion-exchange material in an ultrasonic water bath cleaner. The cleaning includes heating (preferably boiling) the ion-exchange material in solution (preferably acidic, most preferably HCl). Most preferably, the ion-exchange material has at least two surfaces and rinsing comprises (in order): roughening the surfaces of the ion-exchange material; cleaning the ion-exchange material; rinsing the ion-exchange material in water; and boiling the ion-exchange material in an aqueous solution (preferably acidic, such as an HCl solution). Rinsing preferably comprises at least two steps of rinsing and boiling the ion-exchange material in solution (in water, for a sufficient time to completely swell the ion-exchange material). Coating is preferably done with a metal, more preferably a noble metal, and most preferably with platinum, and is performed for a time sufficient to cover the ion-exchange material with a coating of approximately 3.75 $mg/cm^2$ of the coating substance. Coating best comprises: immersing the ion-exchange material; and stirring. Immersing is preferably done into a solution containing a salt of a metal, such as a noble metal, palladium, or nickel, preferably a platinum salt, more preferably a platinum-amine complex, and most preferably $Pt(NH_3)_4Cl_2$. The reducing step best comprises exposing the ion-exchange material to $NaBH_4$. Reducing is preferably done in solution (e.g., aqueous) containing a reducing enhancer such as $NH_4OH$, and involves continuously raising the temperature of the solution to a predetermined temperature. Reducing is best done at an elevated temperature in solution in a water bath at an elevated temperature and includes simultaneously stirring the solution in the water bath, and preferably simultaneously stirring the solution (at low speed) while adding the reducing agent. Most preferably, reducing comprises simultaneously: continuously raising the temperature of the solution to a predetermined temperature; and adding supplementary reducing agent at intervals. This preferably includes maintaining the temperature at the predetermined temperature and simultaneously adding a final amount of supplementary reducing agent when the predetermined temperature is reached, continuously stirring the solution after adding the final amount of supplementary reducing agent, rinsing the ion-exchange material (in water or HCl solution), and storing the ion-exchange material. Preferably, the reducing step comprises at least one reducing step comprising (in order): rinsing the ion-exchange material; immersing the ion-exchange material in a solution containing a reducing agent; rinsing the ion-exchange material; and storing the ion-exchange material. Preferably, the immersing is in a solution (aqueous) containing a salt of a metal such as a noble metal, palladium, or nickel, preferably a platinum salt, more preferably a platinum-amine complex, and most preferably $Pt(NH_3)_4Cl_2$, as well as a reducing enhancer such as $NH_4OH$, as well as a reducing agent such as $H_2NOH.HCl$ or $H_2NNH_2.H_2O$.

Reducing preferably comprises simultaneously: continuously raising the temperature of the solution to a predetermined temperature; and adding supplementary reducing agent at regular intervals for a time sufficient to substantially complete reduction, as well as testing the solution for completion of reduction such as by monitoring a color change produced by reduction. Rinsing preferably involves at least two rinsing steps, the first in water or an acidic (HCl) solution, or both in sequence, and is performed for a time sufficient to exchange cations in the ion-exchange material for H+ cations outside the ion-exchange material. The second is in water or a basic (NaOH) solution, or both in sequence, and is performed for a time sufficient to exchange cations in the ion-exchange material, such as H+ cations in the ion-exchange material are exchanged for alkali metal (Na+) cations outside the ion-exchange material. Preferably, a second of the at least one reducing and the rinsing are repeated, followed by a final rinsing step in water. After the two preferred rinsing steps, the ion-exchange material is preferably cleaned ultrasonically. Storing is preferably done in water.

The invention is also of a method of preparing an actuator comprising: at least one cleaning step; at least one step of rinsing an ion-exchange material; at least one step of coating the ion-exchange material with a substance which undergoes chemical reduction in the presence of a reducing agent; at least one step of reducing the coating on the ion-exchange material by exposing the ion-exchange material to a reducing agent; testing the solution for the completion of reduction; and at least one step of storing the treated ion-exchange material. In the preferred embodiment, the ion-exchange material is an ion-exchange membrane, an ionomer membrane, an ion-exchange resin, a gel, beads, a powder, filaments, or fibers, preferably an ion-exchange membrane, more preferably a polymer ion-exchange membrane, and most preferably a perfluorinated sulfonic acid ion-exchange polymer membrane. Rinsing is preferably done in water or solution (acidic, such as HCl, or basic, such as NaOH), and involves heating (boiling in solution) the ion-exchange material. At least two rinsings are best performed before coating. Coating is preferably done with a metal, preferably a noble metal, palladium, or nickel, and most preferably platinum. Preferably, at least one rinsing occurs before and after each reducing, and the reducing is done in the presence of a reducing enhancer ($NH_4OH$). Exposing is best done to a reducing agent ($NaBH_4$, $H_2NOH.HCl$, or $H_2NNH_2.H_2O$), preferably first to $NaBH_4$, and later to $H_2NOH.HCl$ or $H_2NNH_2.H_2O$. Preferably, reducing is done in solution and includes: heating the reducing solution; continuously stirring the ion-exchange material in the coating solution at low speed; and simultaneously raising the temperature of the solution while adding supplementary reducing agent. Testing preferably includes: mixing a test solution comprising a portion of the reducing solution; boiling the test solution; and detecting a color change in the testing solution during boiling. The portion is preferably about 2 ml and testing includes: adding $NaBH_4$ to the test solution during boiling; and adding supplemental reducing agent to the reducing solution in which the ion-exchange material is immersed if a coloration is detected in the test solution during boiling, and terminating reducing otherwise. Storing is best done in water or in solution (acidic, such as HCl).

The invention is additionally of a method of preparing an actuator from an ion-exchange material comprising: roughening the ion-exchange material; a first step of cleaning the roughened ion-exchange material; a first step of rinsing the ion-exchange material; a first step of boiling the ion-exchange material; a second step of rinsing the ion-exchange material; a second step of boiling the ion-exchange material wherein boiling is performed for a sufficient time to completely swell the ion-exchange material; a step of coating the ion-exchange material with a substance comprising platinum; a third step of rinsing the ion-exchange material; a first step of reducing the coating on the ion-exchange material by immersing the coated ion-exchange material in a solution comprising a reducing agent whereby the coating undergoes chemical reduction in the presence of the solution comprising the reducing agent; simultaneously heating and stirring the ion-exchange material in the reducing agent; a fourth step of rinsing the ion-exchange material; a first step of storing the ion-exchange material; a fifth step of rinsing the ion-exchange material; a second step of reducing the coating on the ion-exchange material by immersing the coated ion-exchange material in a solution comprising a reducing agent whereby the coating undergoes chemical reduction in the presence of the solution comprising the reducing agent; simultaneously heating and stirring the ion-exchange material in the reducing agent; at least one step of sequentially rinsing the ion-exchange material; a second step of cleaning the ion-exchange material; and a second step of storing the ion-exchange material. The steps are preferably performed in the above order, and the last four repeated and including a final rinsing step prior to the second storing step.

The present invention is also of an actuator, produced by any of the above summary methods, comprising a treated ion-exchange material capable of a completely reversible deflection and means operably connected to the ion-exchange material for electrically driving the deflection of the ion-exchange material.

The invention is further of an actuator for use in a gripper mechanism comprising: at least two actuators, produced by any of the above methods, positioned opposite to each other and being capable of bending in equal and opposing directions; a power supply to the actuators to drive the mechanical bending of the actuators in opposing directions; electrical impulse conductors operably attached to the first end of each of the actuators for conducting electrical impulses across the actuators; and wiring, operably attached to the conductors and to the power supply, for electrically connecting the actuators to the power supply.

The invention is additionally of an actuator for providing three-dimensional movement, comprising: three actuators produced by any of the above methods, comprising a hollow triangular tube having a longitudinal axis wherein each of the actuators of the tube comprises a face of the tube; signal conductors, operably attached to the first end of each of the actuators, for conducting a signal across each of the faces of the tube, thereby stimulating each face of the tube at a phase angle apart from each adjacent face to produce a motion around the longitudinal axis of the tube; and a power supply for providing power to the signal conducting means; and a power conductor, attached to the signal conductors, for operably connecting the tube to the power supply. The signal is preferably a low amplitude alternating signal.

The present invention is still further of an actuator for use as a wing flap, comprising: at least two actuators, produced by any of the above methods, sandwiched in series in a stack configuration, each of the actuators formed in a planar layer and capable of acting as a series resistor element; power conductors, operably attached to the stack at the first end and the top and bottom surfaces, for conducting power across the stack; a power supply for supplying power to the stack; and connectors for connecting the power supplying means to the power conducting means. In the preferred embodiment, adhesive is placed between the actuators, preferably conductive and non-continuously applied.

The invention is also of an actuator for use as a robotic swimming structure, comprising: at least two actuators produced by any of the above methods, formed in an ion-exchange material having a first end, the ion-exchange material comprising a plurality of polymer gel fibers imprinted with means for conducting power through the ion-exchange material; conductors, operably attached to the ion-exchange material at the first end, for conducting an alternating low voltage across the ion-exchange material; a power supply for providing power to the conductors; a modulator for modulating speed of bending of the ion-exchange material varying the frequencies of the applied voltage; and a connector for operably connecting the conducting means to the power providing means. In the preferred embodiment, the actuator includes a buoyancy varier for varying the buoyancy of the swimming structure and a sealed housing, operably attached to the ion-exchange material at the first end, the housing comprising a signal generator (erasable programmable chip) and a power generator (a battery). The ion exchange material may be elastic or rigid.

The invention is yet further of an actuator for use as a resonant flying machine, comprising: at least one ion-exchange material actuator, prepared by any of the above methods, in the form of a planar layer having first and second ends, a top surface and a bottom surface; power conductors for conducting power across the ion-exchange material actuator, operably attached to the top and bottom surfaces of the ion-exchange material and along a central axis of the ion-exchange material equidistant from the first and second ends, whereby the ion-exchange material actuator is capable of reversibly bending in a flapping motion upon receiving power; a power supply for providing power to the conductors; and connectors for connecting the conductors to the power supply.

The invention is also of an actuator for use as a guide wire or a micro-catheter in intra-cavity medical applications, comprising: at least one ion-exchange material actuator prepared by any of the above methods, and formed in a small strip; a power supply for providing power to the strip; and connectors for connecting the strip to the power supply.

The invention is also of a sphincter-type or a squeeze-type actuator used in medical applications for incontinence and cardiac-assist devices.

Additional objects, advantages and novel features, and further scope of applicability of the present invention will be set forth in part in the detailed description to follow, taken in conjunction with the accompanying Figures, and in part will become apparent to those skilled in the art upon examination of the following detailed description, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying Figures, which are incorporated into and form a part of the specification, illustrate several embodiments of the present invention and, together with the description, serve to explain the principles of the invention. However, these Figures, as well as the following detailed description and the examples, are only for the purpose of illustrating a preferred embodiment of the invention and are not to be construed as limiting the invention. In the drawings.

Figure 1:
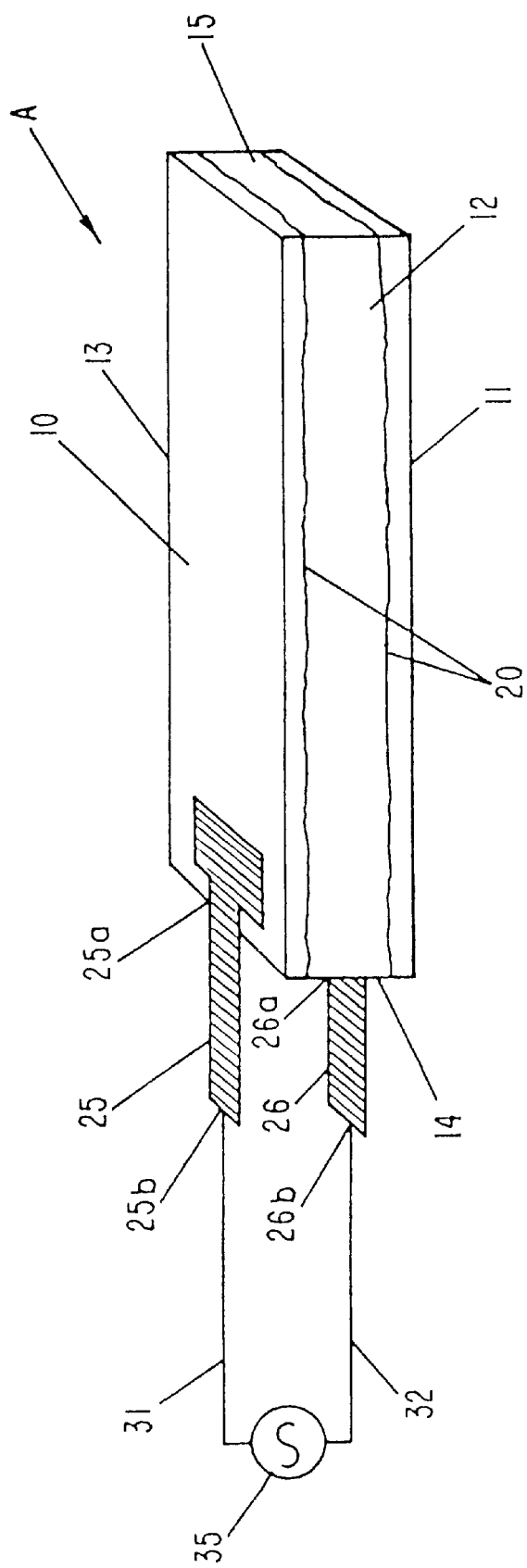
FIG. 1 is a perspective view of the actuator of the invention showing the treated membrane actuator with electrodes placed at one end of the membrane and terminals connected to a power source at the other end.

DESCRIPTION OF THE PREFERRED EMBODIMENTS (BEST MODES FOR CARRYING OUT THE INVENTION)

The invention involves methods of manufacturing, packaging and use of ion-exchange membrane actuators and/or sensors made from ion-exchange membranes (or any ionomer membrane, ion-exchange resin, gel, beads, powder, filaments, or fiber) by chemically, mechanically and electrically treating them with at least one noble metal such as platinum.

A method of the invention of preparing an actuator and/or sensor comprises rinsing a membrane, coating the membrane with a substance which undergoes chemical reduction in the presence of a reducing agent, reducing the coating on the membrane by exposing the membrane to a reducing agent. The proposed manufacturing technique produces a typical flap muscle of 0.2–0.4 mm thickness, 2–5 mm width and 20 mm length which can achieve a completely reversible maximum deflection of 12–15 mm under a maximum voltage of 2.0–2.5 volts. More particularly, in the method for manufacturing actuators and/or sensors according to the subject invention, polymeric ion-exchange membranes are used by a method comprising a first cleaning step, at least one step (preferably two steps) of rinsing a membrane, at least one step of coating the membrane with a substance which undergoes chemical reduction in the presence of a reducing agent, at least one step (preferably two steps) of reducing the coating on the membrane by exposing the membrane to a reducing agent, a second cleaning step, and at least one step (preferably two steps) of storing the treated membrane. Several of these steps, in particular the reducing steps, may be repeated as needed to obtain a desired result.

The invention also includes a number of novel applications, devices, sensors and/or actuators made from this specially treated material. Preferred uses of the treated membrane of the invention include any application requiring noiseless propulsion in water. Further applications include its use as a gripper (tweezers), an three dimensional actuator for use with a generator, a composite wing flap, an autonomous robotic swimming structure, a resonant flying machine, a snake-like robot, a wobble motor, a multifingered robotic hand, a displacement sensor, a blood pressure/stress sensor, and a joint pressure/stress transducer.

The present invention having been generally described, the following preferred specific embodiments are provided to illustrate some of the properties and demonstrate the practical advantages thereof, and to allow one skilled in the art to utilize the present invention to its fullest extent. These examples included are to be construed as merely illustrative, and not limitative of the remainder of the disclosure or the claims in any way whatsoever.

The manufacturing method of the present invention was performed using ion-exchange membranes (or any ionomer membrane) such as a perflourinated sulfonic acid polymer or ionomer such as NAFION® which is a perfluorinated sulfonic acid ion-exchange polymer membrane are used for separation processes, production of caustic sodas and fuel cell application in the industry. Ion-exchange membranes are hydrophilic ionic polymers and swell up to 16% in water at room temperature.

The following lists the step-by-step preparation of an exemplary actuator from a 2 by 2 square inch NAFION® 117 membrane (0.007 inch thick):

1. Both surfaces of the membrane are roughened using a smooth sandpaper (such as Norton 600A). Alternatively, roughening can be accomplished with short bursts of fine glass bead sandblast (2 sec/cm$^2$).
2. The membrane is then cleaned in an ultrasonic water bath cleaner for about 10 minutes.
3. The membrane is rinsed with pure (deionized) water and boiled in a 2.4N aqueous solution of HCl for about 30 minutes.
4. The membrane is again rinsed with pure water and boiled in pure water for about 30 minutes to completely swell the membrane.
5. The membrane is then immersed in a solution of 0.2% platinum-amine complex (Pt(NH$_3$)$_4$Cl$_2$) (tetra-amine platinum chloride hydrate, 98%) for 8 hours at room temperature while slowly stirring the solution. The final amount of platinum deposited on the membrane must be about 3.75 mg/sq cm for each face of the membrane surface. This produces a pair of porous dendritic electrodes on the surface of the membrane,
6. The membrane is then rinsed again with pure water and immersed in a reducing solution consisting of 180 ml H$_2$O, 0.5 ml NH$_4$OH 30%, and 2 ml NaBH$_4$ 5% in a water bath at 40° C. while stirring at low speed (150 RPM). Additions of 2 ml NaBH$_4$ 5% are made every 30 minutes for about 3 and a half hours while gradually raising the temperature to 60° C., at which point 20 ml NaBH$_4$ 5% is added, and the mixture is stirred for an additional one and a half hours. Then the membrane is rinsed with pure water and stored in a 0.5% solution of HCl for 8 hours.
7. Following its removal from storage, the membrane is again rinsed with pure water and immersed in a solution containing 300 ml H$_2$O, 0.2 grams Pt(NH$_3$)$_4$Cl$_2$, 3 ml H$_2$NOH.HCl 5% (hydroxylamine hydrochloride, 99%), 1.5 ml H$_2$NNH$_2$.H$_2$O 20% (hydrazine monohydrate, 98%), and 0.5 ml NH$_4$OH 30% at 40° C. while stirring at low speed (approximately 60 RPM). Reducing agents consisting of 3 ml H$_2$NOH.HCl 5% and 1.5 ml H$_2$NNH$_2$.H$_2$O 20% were then added every 30 minutes for 4 hours while gradually increasing the temperature to 60° C. After the process is over, the solution containing the membrane was tested for any residual Pt by boiling 2 ml of the solution with 2 ml NaBH$_4$ 5%. If the color of the mixture turns black, the addition of reducing agents must continue for longer time. If no color change is visually detected, the process is complete. Step 7 is part of the developing process to deposit more platinum in the polymer matrix.
8. When reduction is complete, the membrane is rinsed with pure water and then with 0.1N HCl solution to remove any other cations in the membrane. Steps 7 and 8 are necessary to insure high level of activity in the final actuator.
9. The membrane is rinsed again with pure water and then with 0.1 N NaOH solution to replace H+ cations in the membrane with Na+ cations.

10. The membrane is then cleaned in an ultrasonic cleaner for 5 seconds and removed.
11. Steps 7, 8, and 9 are repeated and followed by rinsing with pure water. The membrane is then stored in pure water at room temperature. Step 10 repeats the developing process to increase the amount of platinum deposited. If one starts out with a higher concentration of platinum salt in step 7, it is possible to deposit sufficient platinum on the membrane on the first pass, thereby eliminating the need for step 11. However, this will increase the risk of oxidation as well as crowding phenomena on surfaces of the membrane in a short time period.

A flap muscle with dimensions of 0.2–0.4 mm thickness, 5 mm width and 40 mm length is typically cut from sheets of 100 mm×150 mm membrane muscles produced by the performance of the above-described steps. This muscle can achieve a completely reversible maximum deflection of 22–25 mm under a maximum voltage of 2.0–2.5 volts and provides noticeable power to weight ratio at low voltages to perform useful work. A major advantage is that one can cut any shape and size muscle from the sheet. In particular, micro-muscles in down to approximately 200 microns in length and 40 microns in width may be cut from such sheets.

FIG. 1 depicts such an actuator made by chemically and mechanically treating NAFION® membranes with platinum according to the method of the invention. FIG. 1 is a perspective view of a treated membrane actuator A in planar form comprising a top surface 10, bottom surface 11 (not shown), sides 12 (shown) and 13 (not shown), a first end 14 (not shown) and a second end 15. As shown, electrodes 20 extend through sides 12 and end 15. Preferably, electrodes 20 are platinum. At end 14, terminals 25 and 26 are attached at their first ends 25a and 26a, respectively, to top surface 10 and bottom surface 11 of actuator A. Terminals 25 and 26 at their second ends 25b and 26b, respectively are connected by wires 31 and 32, respectively, to a power source 35.

Membrane actuators can be manufactured and packaged for specific applications. These actuators produce a bending motion when placed in a low voltage electric field. The membrane always bends toward the anode and then back to cathode and null position when a low voltage is applied and removed sequentially. The bandwidth of the membrane depends on its size and geometry; for the typical actuator, the bandwidth is about 40 Hz. Also, for the typical actuator produced by the method above, the current across the membrane is about 100 mA/sq cm, and the applied voltage necessary for actuation is about 1.5–2.5 volts. The most important aspect here is to chemically deposit (or coat) porous (perforated) platinum electrodes on the membrane surface with some penetration inside the membrane across its thickness. For purposes of the specification and claims, "coating" is defined as depositing a layer (porous or non-porous), when used as a verb, and as a deposit (porous or non-porous), when used as a noun.

The actuators and sensors of the invention are hydrophilic and operate in moist environments. Therefore, for application in open-air systems, they are preferably encapsulated in an elastic membrane such as latex.

Sensors fashioned from polyelectrolyte and/or ionic polymers of the present invention sense motion related parameters such as force, acceleration, velocity, vibration, and displacement by their generation of a corresponding voltage signal in the range of a few millivolts. Unlike piezoelectric devices or strain gauges, the composite membranes of the present invention sense large motions and respond to shock loading. Furthermore, the signal produced by the sensor membranes responds to the rate dependence of applied forces. The sensors of the present invention also sense torsional forces. Overall, complex electronics are not needed to capture the signal generated by the applied force. The sensors of the present invention also have a very broad bandwidth and can sense oscillatory motion at rates of up to hundreds of Hz, unlike most polymeric gels. The sensors presented herein respond to stimuli of differing amplitudes and frequencies, providing an output voltage signal that closely follows the applied motion or force. Thus, the sensors serve adequately as large motion strain gauges when mounted to a structure undergoing large motion or subject to large forces. In addition, when combined with an actuator, or when used as an actuator itself, the sensor, or sensor/actuator, provides feedback, for use in controlling the actuator or sensor/actuator device. Such embodiments of the present invention prove useful in numerous applications, such as intelligent system control or heart-assist devices. Such a heart-assist device comprises a number of composite membranes arranged around the heart, especially the left ventricle, to provide pumping assistance; however, other configurations are possible. In such applications of the sensors, feedback is derived from the motion of the membranes or force encountered. Supplemental pumping is accomplished by wrapping membranes around an artery or vein and applying a pulsed contraction or a traveling wave to the device. Such applications of the present invention can, in addition, or instead, provide feedback to the entire pumping system.

Sensor embodiments of the present invention are made in a manner as described above. Strips of sensor composites cut in a standard size are capable of undergoing large bending displacement when placed in a low electric field or under influence of an applied force. Thus, by bending a sensor strip, an electrical potential arises across the sensor electrodes, or a sensor electrode and a reference electrode. Calibration of the output voltage provides for a standard size sensor that is correlated to the applied loads or stresses; although, some sensor embodiments of the present invention showed a hysteresis curve for a complete cycle of bending. All curves show a region having a relatively linear relationship between output voltage and displacement. Furthermore, unlike strain gages where the output voltage needs to be conditioned and amplified by a factor of 1000 or more, sensors of the present invention can produce up to millivolt output and sense large deformations. Thus, small amplifier gains of two orders of magnitude less than conventional sensors are useable. Sensors of the present invention are capable of fabrication from several microns to several inches in dimension for various applications. Also they do not have shortcomings and other limitations associated with bonding of typical strain gages to a surface. An advantage of sensors of the present invention is use for large motion sensors and/or actuators. Simple feedback control scheme and double layers of the composite film allow for use as self-contained robotic manipulators that do not need sophisticated sensors modules for full integration of intelligence.

A simple theory for deformation regimes of a composite sensor in a static mode where the composite deformation is evaluated for loads at given deformation intervals helps to explain phenomena associated with sensor and actuator operation. The model, derived from geometric constraints and nonlinear elasticity theory, applies for large deformations provided that no approximation is made to resulting differential equations describing field displacement. The proposed theory uses a "rubber elasticity" formulation for very large deformations as applied to our composite sensor.

Figure 12:
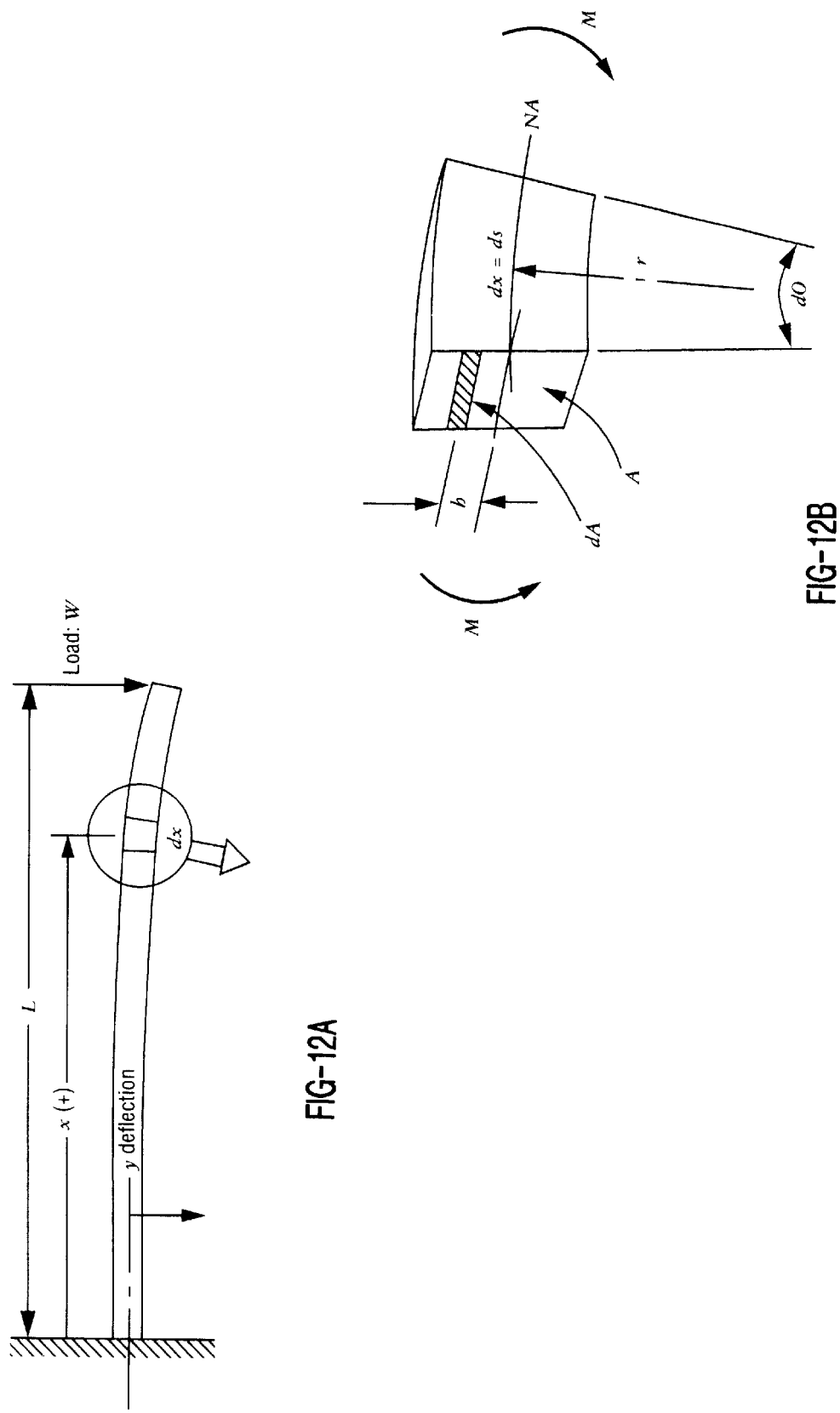
FIG. 12 is a schematic of a simple cantilever beam configuration for a sensor analysis.

Consider a simple cantilever beam with uniform rectangular cross section with an area A as shown in FIG. 12. The beam is fixed at x=0 and assumed to have a concentrated load W at the free end where x=L and its deflection is measured in the y direction from unloaded neutral axis. The modulus of elasticity of the beam material is E. The relationship for displacement of the beam at any point along the beam and applied load can be obtained using a nonlinear elasticity.

Experimental results showed that the tip displacement in the positive direction was linearly related to output voltage of the sensor; results are described in an example.

Sensors of the present invention can behave as viscoelastic materials or springs. In simple spring mechanics, a spring constant characterizes the relationship between displacement and applied force. Similarly, the "spring constant" approach is applicable to operational characteristics of the present invention. In particular, application of an electrical potential across a membrane electrode and another point will alter the membrane's "spring constant." Rheologically, the same phenomena are describable in more complex viscosity terms through an examination of stress, force, momentum, etc. A further degree of complexity is introduced by characterizing sensors and/or actuators of the present invention in terms of chemical, electrical and/or heat transfer phenomena. The ability to actively and beneficially control such phenomena is an integral advantage of various embodiments of the present invention.

Another preferred embodiment of the present invention uses output from a sensor to feedback information to an actuator, other device, or even the sensor itself. For instance, a signal from a sensor can feedback as a voltage to alter the material properties of the sensor, e.g., properties such as "spring constant" or rhelogical properties. A sensor/actuator feedback loop also serves as a stress or force indicator wherein the sensor/actuator position is maintained constant or set to programmed positions by application of a feedback to alter the electrical potential of the membrane-based device.

As sensors, the present invention fills the need for enhanced blood pressure (BP), pulse rate and rhythm sensors. Sensors of the present invention measure systolic and diastolic BP, pulse rate and rhythm. The sensors of the present invention take advantage of various physical phenomena that convert normal and shear load inputs into an induced voltage output across a sensor's thickness. The sensors are also suitable for installation on the inner surface of a cuff to measure systolic and diastolic BP, pulse rate, and rhythm. An added benefit is the ability of measuring "pulse rhythm" which gives a more amplified look at heart irregularities that typical pulse rate sensors are unable to show. The sensors of the present invention produce consistent and reliable BP readings, pulse rate, and rhythm. Typically, a linear relationship between applied maximum load and induced maximum voltage is obtained, which can be easily translated into good BP reading.

In another embodiment of the present invention, the device is used as a sensor to measure the pressure distribution and motion within the human spine, for both in vivo and in vitro situations. Of course this embodiment is also useful as a sensor in other parts of the body. In particular, the sensor of the present invention is useable for measuring pressure/stress in joints, such as, but not limited to, hip, shoulder, wrist, mandible, hand and foot. This embodiment of the present invention, as applied to spines, uses small thin strips of ionic polymer-metal composites, pressure/stress transducers for the quantification of pressure distributions within the spine. Due to their small size, IPMC sensors have the benefit of being able to fit within small gaps in the spine. These fluid-filled gaps (facet joints) range in thickness from 1 mm to 3 mm, which is generally too small for typical transducers. Biocompatibility issues of these sensors themselves, although relatively biologically inert, can be overcome by coating with various flexible biocompatible materials.

Overall, biomechanics of the human spine is one area of research that often requires the need for pressure instrumentation. Sensors of the present invention overcome problems associated with many pressure transducers that exist for recording variations in stress distributions within the spine. In particular, the present invention overcomes bulkiness of transducers that cannot be implemented in certain regions of the spine because of their size. The sensors of the present invention also overcome limitations inherent in many transducers due to malfunctioning if the electronics of the transducer are exposed to fluid, thereby requiring encapsulation and sealed prior to use. A major problem in pressure sensing devices results from diffusion of water into the transducer resulting in unpredictable zero, or baseline, drift. Therefore, special attention must be paid to the sealing of the transducer to improve the stability of its readings. The sensors of the present invention use thin IPMCs that function as pressure transducers where the presence of fluid tends to enhance the performance by maintaining isothermal conditions and moisture levels advantageous to operation. The ability to make sensors of 0.2 mm thickness is advantageous because it allows pressure measurement within the facet joints, spinal canal, anterior and posterior ligamentous tissues, and other regions that may be difficult to attain due to their limited space. The sensors of the present invention are customizable by size and other aspects according to the application, for instance, for recording pressures within intervertebral disc regions of the spine to understand how the degenerative processes, such as aging, of the intervertebral disc alters the normal loading pattern of the spine.

INDUSTRIAL APPLICABILITY

The invention is further illustrated by the following non-limiting examples.

The following examples are additional embodiments of the present invention and illustrate novel applications of the artificial muscles and actuators resulting from experiments using the method of manufacturing of the subject invention.

EXAMPLE 1

Membrane Grippers

Figure 2:
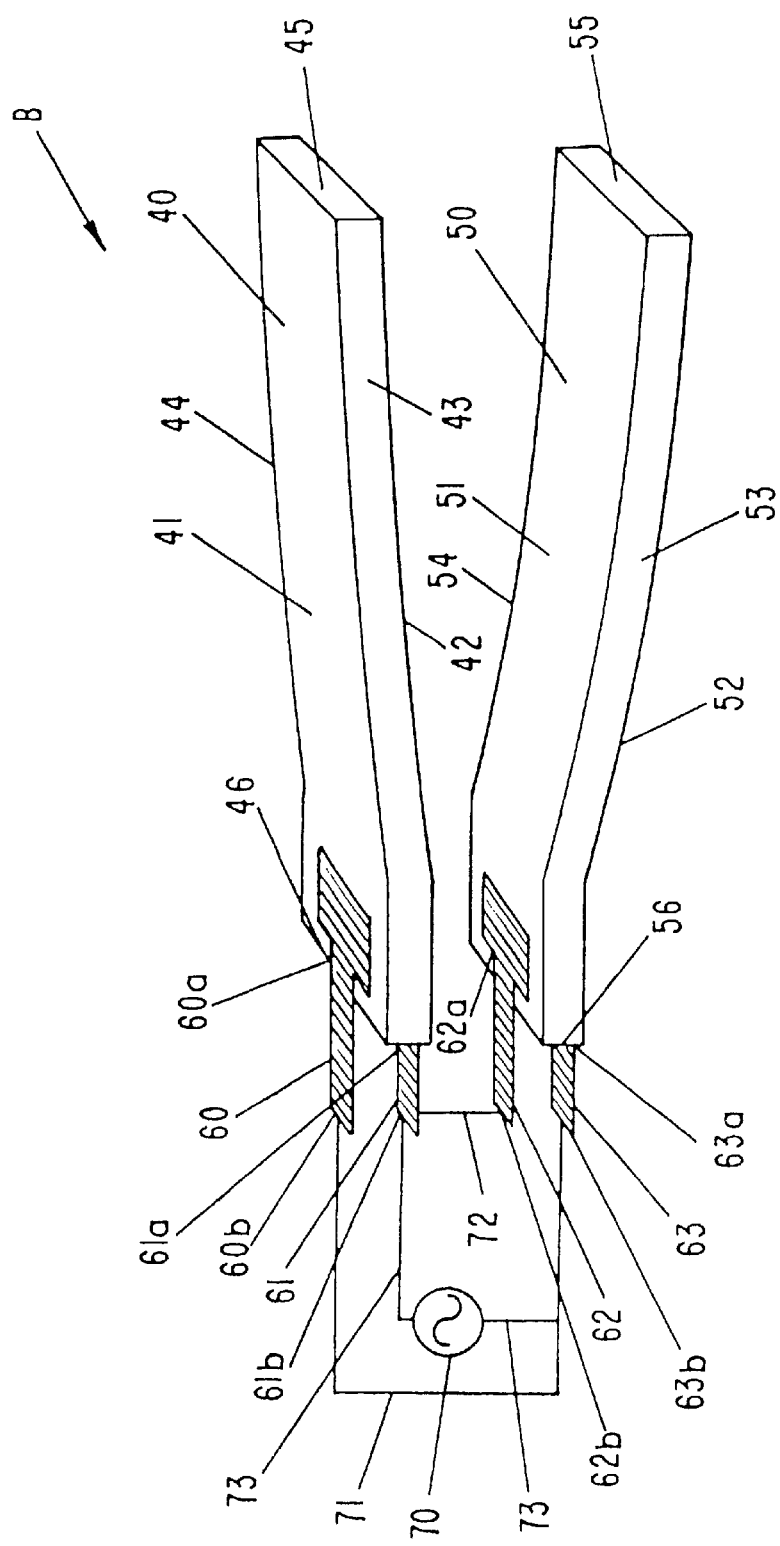
FIG. 2 is a perspective view of the actuator of the invention showing use of the treated membrane actuator as an electrically controlled tweezer with terminals connected to a power source at one end.

The membrane can be fabricated to act as a micro- or macro-gripper, e.g., tweezers, for gripping action when two membranes are wired and sandwiched in a way so that they bend in opposing direction. FIG. 2 is a perspective view of an embodiment of the invention showing two treated membrane actuators 40 and 50 packaged as an electrically controlled gripper B. Actuators 40 and 50 each comprise respectively top surfaces 41 and 51, bottom surfaces 42 and 52 (not shown), sides 43 and 53 (shown), sides 44 and 54 (not shown), first ends 45 and 55 (shown) and second ends 46 and 56 (not shown). Actuators 40 and 50 are disposed opposite to each other with bottom surface 42 of actuator 40 facing top surface 51 of actuator 50. The first ends 60*a* and 61*a* of terminals 60 and 61 are attached to the top surface 41 and the bottom surface 42, respectively, at the second end 46 of actuator 40, and the first ends 62*a* and 63*a* of terminals 62 and 63 are attached to the top surface 51 and the bottom surface 52, respectively, at the second end 56 of actuator 50. Terminals 60 and 63 are connected to each other and to one pole of the power supply 70 by electrical wire 71 attached to their ends 60b and 63b, respectively. Terminals 61 and 62 are connected to each other by electrical wire 72 attached to their ends 61b and 62b, and to the other pole of the power supply 70 by electrical wire 73, respectively. The length of wire 72 depends on the required gap between the two actuators 40 and 50 depending on application.

EXAMPLE 2

Three-dimensional Membrane Actuator

Figure 3:
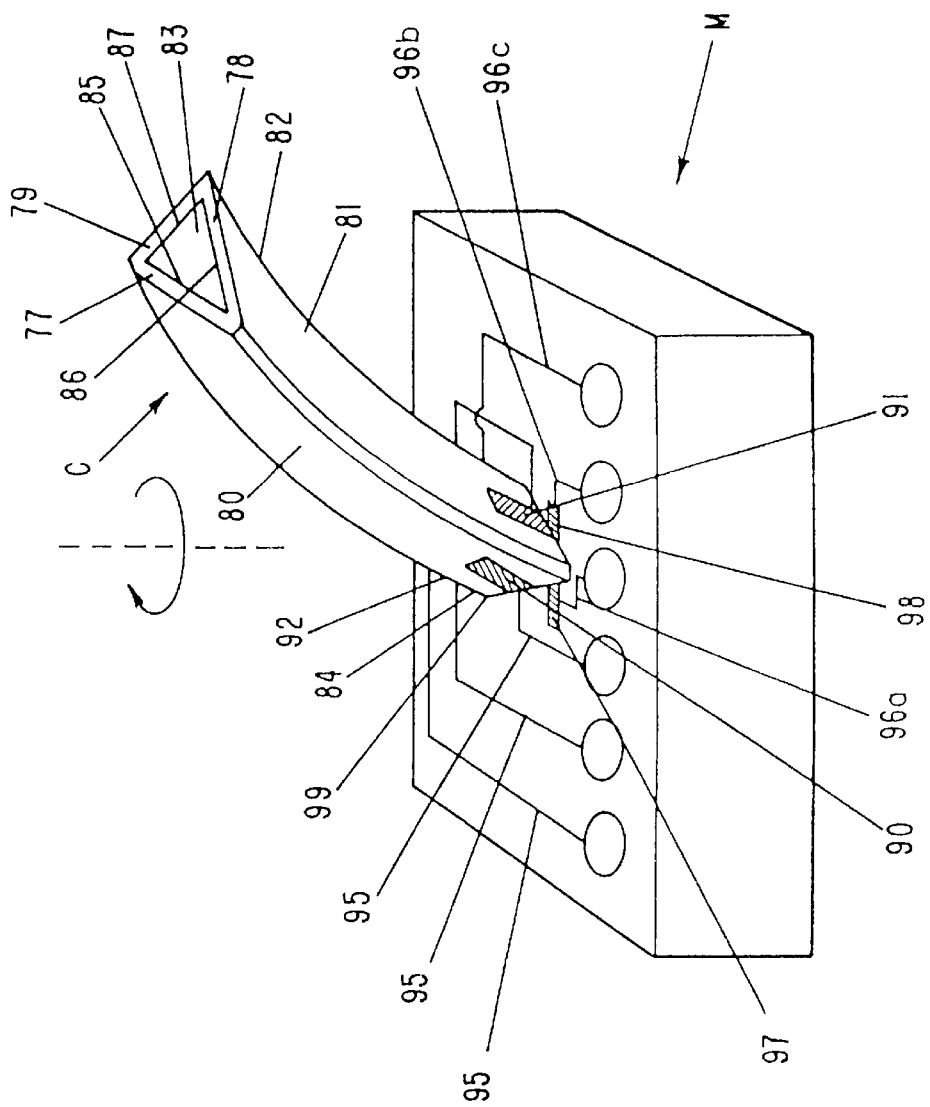
FIG. 3 is a perspective view of the actuator of the invention showing the treated membrane actuator packaged in three-dimensional form for use with a three-phase generator box. Terminals are disposed at the end of the actuator positioned nearest the generator box.

FIG. 3 is a perspective view of a three-dimensional membrane actuator C packaged in three-dimensional form for use with a three-phase generator box M. Actuator C comprises a hollow triangular tube configuration consisting of three independent membrane actuators 77 (shown), 78 (shown) and 79 (partially shown) attached and electrically insulated along the long edges with three external faces 80 (shown), 81 (shown) and 82 (not shown), respectively and a first end 83 (free) and second end 84 which is fixed to the generator box M. External terminals 90 (shown), 91 (shown), and 92 (not shown) are disposed at the second end 84 of actuator C for connection to electrodes 95a (shown), 95b (shown), 95c (shown), respectively incorporated in generator box M. Internal faces of the actuators 85 (not shown), 86 (not shown), and 87 (shown) are connected via internal terminals 97 (partially shown), 98 (partially shown) and 99 (not shown) to electrodes 96a (shown), 96b (shown) and 96c (shown) of the generator box M, respectively. Membrane actuator C is fabricated to produce a 3-dimensional movement by positioning each of actuators 77, 78, and 79 to be stimulated at a phase angle apart from the adjacent actuator by a low amplitude alternating signal, therefore inducing wobble-like motion around the long imaginary axis of the combined actuator tube in null position.

In FIG. 3, the three actuators 77, 78, and 79 are joined together by a flexible adhesive (such as LOCTITE SUPERFLEX™) at the edges (seams). Each actuator has its own terminal connections to each phase of a typical 3-phase power generator (M) or a multi-phase power supply (programmable function generators/power supplies exist that have phase-separated outputs). Each of these actuators has its external and internal faces similar to the top and bottom faces of the tweezer shown in FIG. 2. The final actuator, then, looks like a triangular hollow tube fixed at one end to a platform and free at the other end to wobble or rotate around an imaginary vertical axis. Each output pair of the 3-phase generator is connected to an input terminal pair of each actuator. Each actuator has a pair of terminals (one on the inside and one on the outside of the actuator). FIG. 3 illustrates this arrangement.

EXAMPLE 3

Composite Wing-Flap

Figure 4:
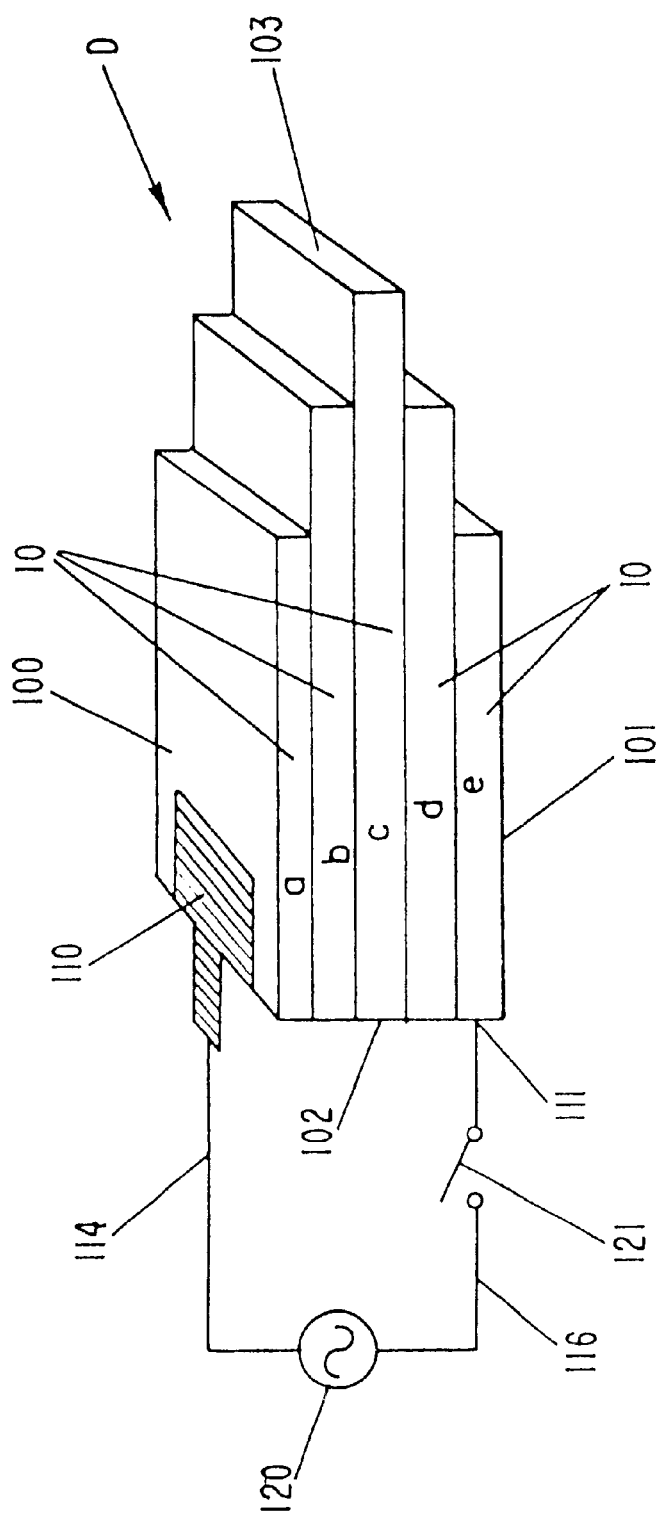
FIG. 4 is a perspective view of the actuator of the invention showing multiple, stacked treated membrane actuators in a composite structure with terminals connected to a power source at one end to be used as a composite wing-flap.

FIG. 4 is a perspective view showing multiple, treated membrane actuators in a stacked (sandwiched), configuration D which is designed to accommodate more power for specific actuations. Actuators 10a, 10b, 10c, 10d, and 10e are each independent planar actuators of different lengths (to provide different stiffness, and therefore resonant frequency, of the composite wing) manufactured according to the process of the invention and formed in a stacked configuration D which as a whole comprises a top surface 100 (shown), a bottom surface 101 (not shown), a first end 102 and a second end 103. Terminals 110 and 111 are connected to top surface 100 and bottom surface 101, respectively, at first end 102 of actuator D. Terminals 110 (shown) and 111 (not shown) are also connected by electrical wires 114 and 116, respectively, to a power source 120. Electrical wire 116 contains an on-off switch 121. Several of these membrane actuators 10 can be assembled in series and multiple amounts of voltage applied to increase power in the composite actuator. Actuators 10a–e act as series resistor elements especially at higher frequencies.

The actuator of FIG. 4 is a resistive element by nature. Therefore, as one stacks several of the actuators, in effect one increases the overall resistance of the combined system. This in turn can allow for higher input voltages. The variation in length of each actuator is due to the desired stiffness of the wing as a whole. Since each actuator has conductivity through its thickness, there is no need to connect wires to faces. By just stacking them one can produce a thicker and more powerful actuator that can handle higher loads. The only necessary terminal connections are on the top face 100 of the top layer 10a and the bottom face 101 of the bottom layer 10e to an alternating (oscillating) source of voltage.

EXAMPLE 4

Robotic Swimming Structure

Figure 5:
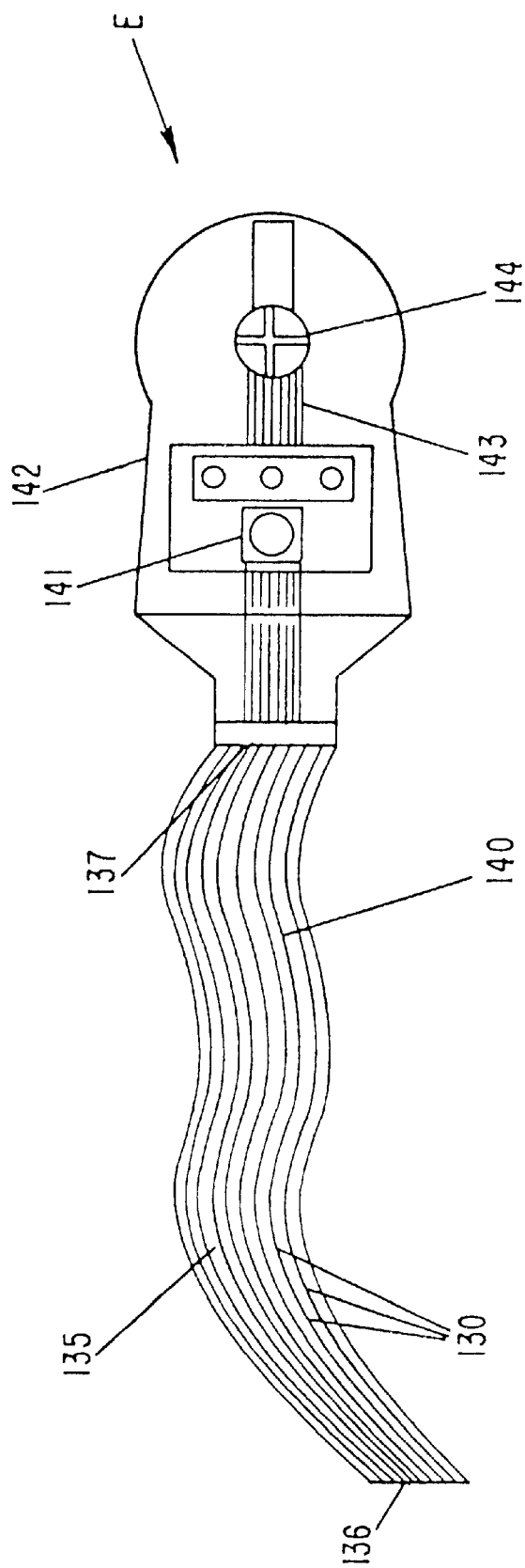
FIG. 5 is a schematic view in elevation of the actuator of the invention showing the treated membrane actuator in elastic form with imprinted electrodes for use as a robotic swimming structure. The membrane is connected to an electronic guidance and control system at one end.

FIG. 5 shows one embodiment of a robotic swimming structure made by cutting and packaging strips of treated ion-exchange membranes 130 to desired size and shape and consequently placing an alternating low voltage (1.5–2.5 V-peak per strip) across the muscle assembly E as shown. In this Figure, muscle assembly E is formed of said polymer gel strips 130 which may be encapsulated into an elastic membrane 135 with electrodes 140 (not shown) imprinted on each strip therein and with a first end 136 (free) and a second end 137 (fixed). Second end 137 is attached to an appropriate electronics and wiring structure 141 for providing guidance and control to actuate the muscle assembly E. Structure 141 as shown comprises a sealed housing module 142 containing therein a means for generating a signal 143 and a means for generating power 144. The tail assembly consists of electrically actuated artificial muscles such as ion-exchange membranes cut in tiny fibers or strips. The tail is then encapsulated in an elastic membrane. The ends of fibers closer to the head assembly 142 are wired to a miniature printed circuit board (PCB) or like assembly to a signal generator assembly consisting of an oscillator circuit and batteries or other power source. The head assembly is preferably sealed to protect the circuitry and electronics from the elements.

By varying the frequency of the applied voltage to the membrane muscle, the speed of muscle-bending oscillation of muscle assembly E, and therefore propulsion of the swimming structure, can be modulated. In this manner, robotic swimming fishes and submarine structures containing a sealed signal and power-generating module (preferably in the head assembly) can be made to swim at various depths by varying the buoyancy of the structure by conventional means. Remote commands via radio signals can then be sent to modulate propulsion speed and buoyancy by radio controls.

EXAMPLE 5

Robotic Fish

Figure 6:
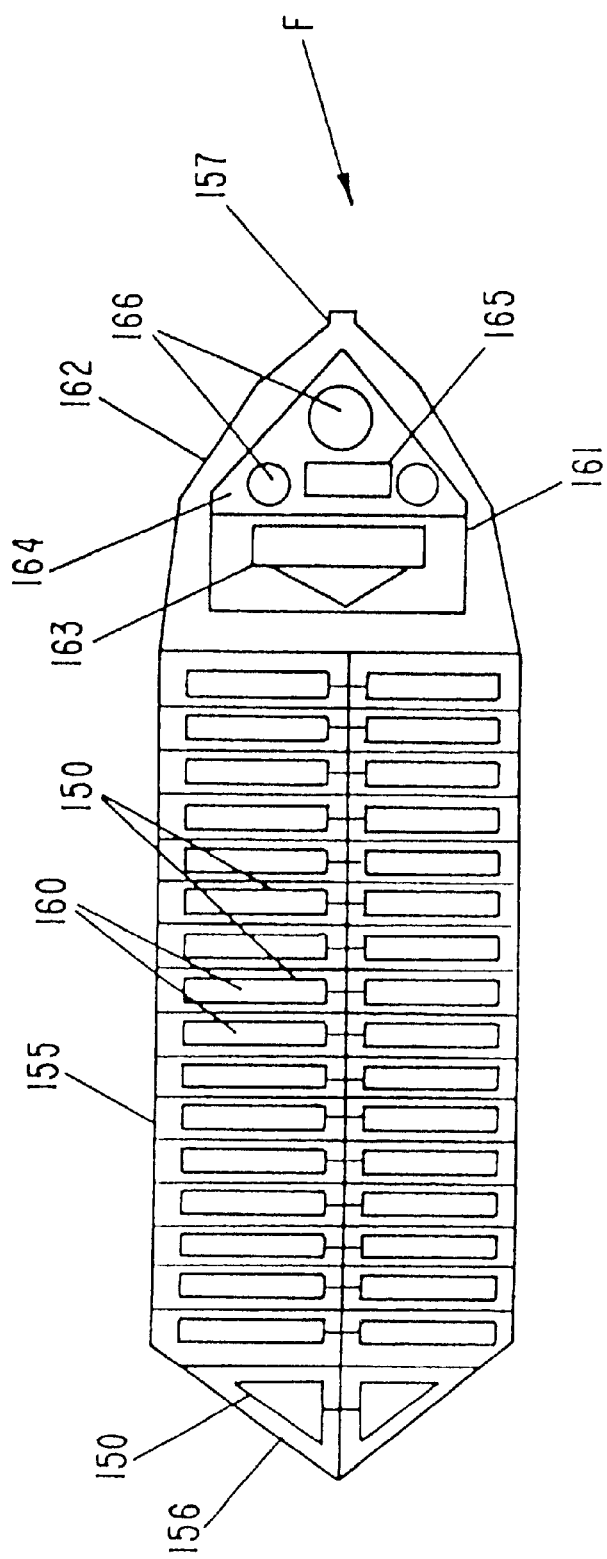
FIG. 6 is a plan view from the top of the actuator of the invention showing the treated membrane actuator imprinted with multiple electrodes spaced throughout and formed in a single rigid structure with the power source at one end. The actuator packaged in this form is suitable for use as a robotic fish.

FIG. 6 is a plan view of the actuator of the invention showing another embodiment of the treated membrane actuator in a elastic construction with imprinted electrodes for use as a robotic swimming structure, more specifically a robotic fish. FIG. 6 shows a robotic swimming structure made by cutting and packaging strips of treated ion-exchange membranes 150 in two rows of desired size and shape and imprinted with electrodes 160 spaced throughout and in a single structure. In this Figure, muscle assembly structure F is formed of said polymer gel strips 150 that may be encapsulated into an elastic membrane 155 with multiple electrodes 160 imprinted therein and with a first end 156 (tail) and a second end 157 (head). Head assembly 157 contains appropriate electronics and wiring structure 161 for providing power, guidance and controls to the muscle assembly F. Structure 161 is contained in a sealed housing module 162, containing therein a means for generating a signal 163 and a means for generating power 164. The power source 164 at end 157 places an alternating low voltage (1.5–2.5 V-peak per strip) across the muscle assembly F as shown. Power source 164 includes an erasable, programmable (EPROM) chip 165 and batteries 166. Note the two rows of small actuators in parallel. Each has two terminals that are connected individually to the multi-phase signal generator 163 located in the head assembly 157. There are also batteries (or other power source) housed in this section for required voltage input. By energizing one pair (across) of actuators at a time and then the consequent pairs downstream, one can produce a propagating or traveling wave downstream on each side of the fish. This will produce a sting-ray type of motion which propels the swimming structure forward. The middle terminals or spines act as conductors that connect the signal generator outputs in the head assembly to each actuator in the tail or wing assembly.

By varying the frequency of the applied voltage, the speed of muscle-bending oscillation of the membranes 150, and therefore propulsion of the swimming structure F, can be modulated. In this manner, robotic swimming fishes and submarine structures containing a sealed signal and power-generating module (preferably in the head assembly) can be made to swim at various depth by varying the buoyancy of the structure by conventional means. Remote commands via radio signals can then be sent to modulate propulsion speed and buoyancy by radio controls.

EXAMPLE 6

Resonant Flying Machine

Figure 7:
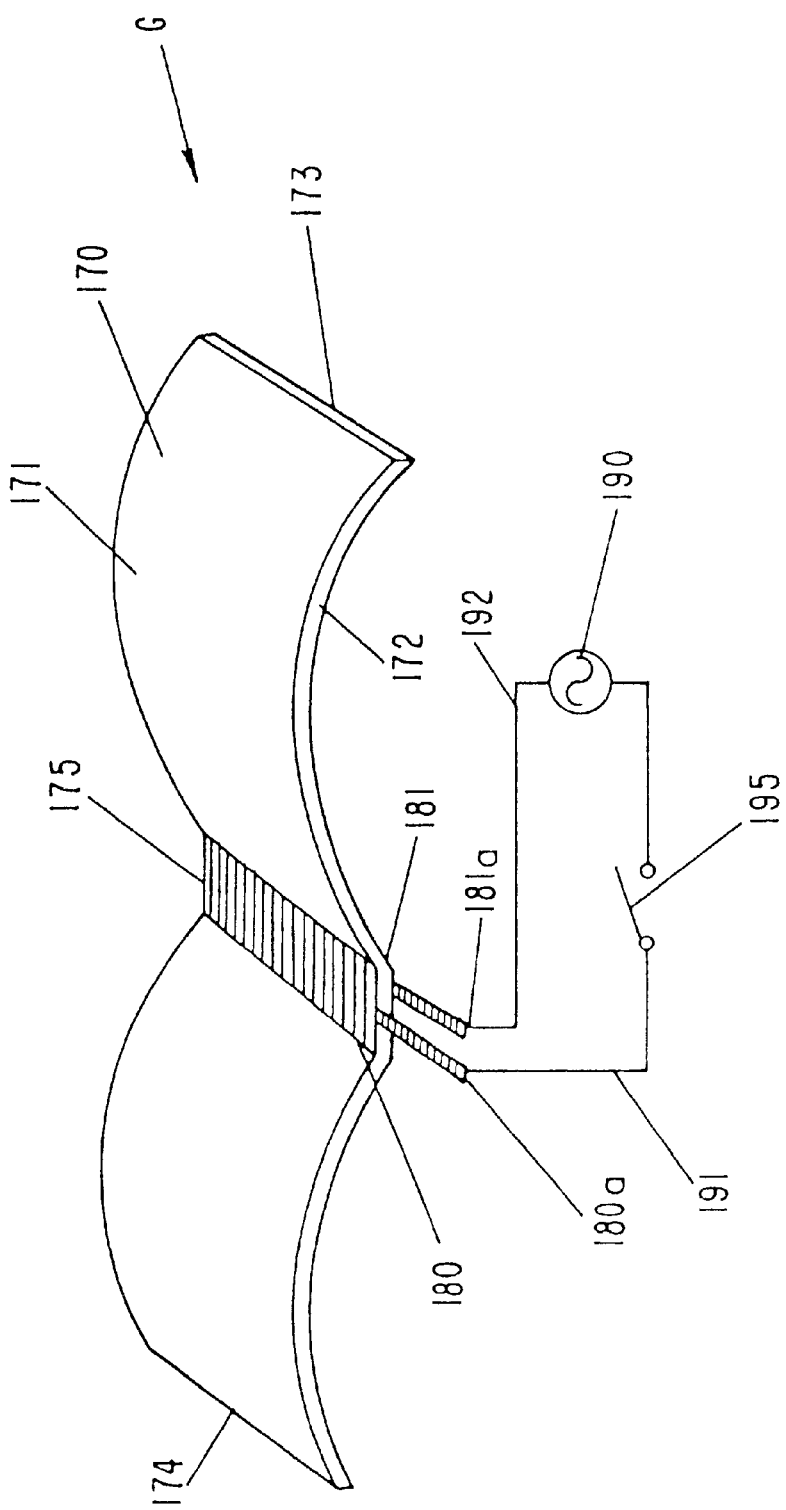
FIG. 7 is a perspective view of the actuator of the invention showing the treated membrane actuator with terminals extending through a central axis of the membrane and connected to a power source. The membrane is packaged in this form for application as a resonant flying machine.

FIG. 7 is a perspective view of the actuator of the invention showing a flying machine G constructed from treated membrane actuator 170 formed in a single sheet having a top surface 171 (shown), a bottom surface 172 (not shown), a first end 173, a second end 174 (not shown) and a central axis 175. Terminal 180, attached to top surface 171, extends along the central axis 175 of the membrane 170 equidistant from first end 173 and second end 174, and diametrically opposed terminal 181 (not shown), attached to bottom surface 172, extends along the central axis 175 of the membrane 170 equidistant from first end 173 and second end 174. Terminals 180 and 181 are connected at their ends 180a and 181a to a power supply 190 by electric wires 191 and 192 respectively. As shown, wire 191 connecting terminal 180 to power supply 190, includes an on-off switch 195.

The membrane is packaged in this form for application as a resonant flying machine. In this configuration, the treated membranes ("muscles") can flap like a pair of wings and create a flying machine. "Resonant" means excitation at the resonant frequency of the membrane, which causes the most violent vibration of the membrane. Each body of mass has a resonant frequency at which it will attain its maximum displacement when shaken by some input force or power. To obtain large displacements of the actuator, one should apply oscillating signals at a frequency close to its body resonant frequency.

In FIG. 7 one sees a large actuator strip with a pair of electrodes (terminals) in the middle fixed to the actuator surfaces of top and bottom. By connecting the circuit to an AC-power source (alternating current signal generator), one can produce oscillating motion of the membrane actuator similar to a hummingbird's or insects wing-flap motion. Furthermore, if one applies the input voltage signal at or near the resonant frequency of the wing structure, large deformations can be obtained which will vibrate the wing structure in a resonant mode. The wing assembly is preferably encapsulated in a thin elastic membrane to prevent dehydration of the actuator.

EXAMPLE 7

Surgical Tool

The actuator can also be used as a guide wire or a micro-catheter in biomedical applications for intra-cavity endoscopic surgery and diagnostics. Small internal cavities in the body can be navigated by using these membrane actuators when used in small strips.

EXAMPLE 8

Metering Valves

Metering valves may be manufactured from the membrane of the invention, the size of an inside dimension plus required tolerances, for any tube that will permit control of aqueous fluid flow by varying the degree of bending displacement of the membrane and applying a calibrated amount of direct current.

EXAMPLE 9

Bellows Pumps

Bellows pumps can be made by attaching two planar sections of slightly different sizes of membrane sections and properly placing electrodes on the resulting cavity. This gives rise to modulating the volume trapped between the membranes when the applied voltage amplitude and frequency is set properly in order to control the flow and volume of fluid being pumped.

EXAMPLE 10

Peristaltic Pumps

Peristaltic pumps can be made from tubular sections of the membrane of the invention and placement of the electrodes in appropriate locations. Modulating the volume trapped in the tube is possible by applying appropriate input voltage at the proper frequency.

EXAMPLE 11

Microelectromechanical Systems

A variety of microelectromechanical systems (MEMS) can be made by packaging and fabricating the membranes of the present invention in small, miniature, and micro sizes. Some examples include biomedical applications such as active microsurgical tools as well as biomimetics such as micro-propulsion engines for material transport in liquid media. Other applications will involve micro-pumps, micro-valves, and micro-actuators. Flagella and cilia type actuators fall under this category.

EXAMPLE 12

Electromechanical Relay Switches

Non-magnetic, self-contained, electromechanical relay switches can be made from the membranes of the present invention by incorporating their bending characteristics in small applied voltages to close a circuit because they are also good conductors. In this manner, several of these actuators can be arranged to make a multipole-multithrow relay switch.

EXAMPLE 13

Artificial Smooth Muscle Actuators

Artificial smooth muscle actuators similar to biological smooth muscles can be made by attaching several segments of tubular sections from membranes of the present invention and employing a simple control scheme to sequentially activate each segment to produce a traveling wave of volume change in the combined tube sections. This motion can be used to transport material or liquid contained in tube volume. The activation of each segment is similar to the peristaltic pump, above. Artificial veins, arteries, intestines made with the membrane of the present invention can be fabricated and packaged in variety of sizes depending on the application.

EXAMPLE 14

Artificial Sphincter and Ocular Muscles

Artificial sphincter and ocular muscles can also be made from the membrane of the present invention by incorporating thin strips of the actuators in a bundle form similar to the parallel actuator configuration. A typical application is in treatment of incontinence.

EXAMPLE 15

Artificial Ventricular or Cardiac-Assist Muscles

Artificial ventricular assist type muscles can also be made for heart patents with heart abnormalities associated with cardiac muscle functions.

EXAMPLE 16

Continuous Variable Aperture Mirrors and Antenna Dishes

Continuous variable aperture mirrors and antenna dishes can be made by cutting circular sections of the membrane of the present invention and placing electrodes at strategic locations. The focal point of the resulting parabolic dish can be varied by strategic placement of the electrodes and varying the amplitude of the applied voltage.

EXAMPLE 17

Linear Actuators

Linear actuators can be made to produce a variety of robotic manipulators including platform type or parallel platform actuators.

EXAMPLE 18

Slithering Device

Snake-like locomotion can be accomplished by arranging proper segments of the membrane of the invention in series and controlling each segment's bending by applying sequential input power to each segment in a cascade mode.

EXAMPLE 19

Parts Orientation/Feeding

Soft parts orientors or feeders for delicate handling of parts in a manufacturing assembly line can be made from flaps made out of the membrane of the invention.

EXAMPLE 20

Incontinence Assist Devices

Various configurations of the muscles of the invention may be used in medical applications involving incontinence. In these systems, a patent can activate the muscles by means of a push-button switch, or the like, to prevent leakage and control discharge by pressing the switch, which is preferably battery operated.

EXAMPLE 21

Displacement Sensor Devices

Figure 8:
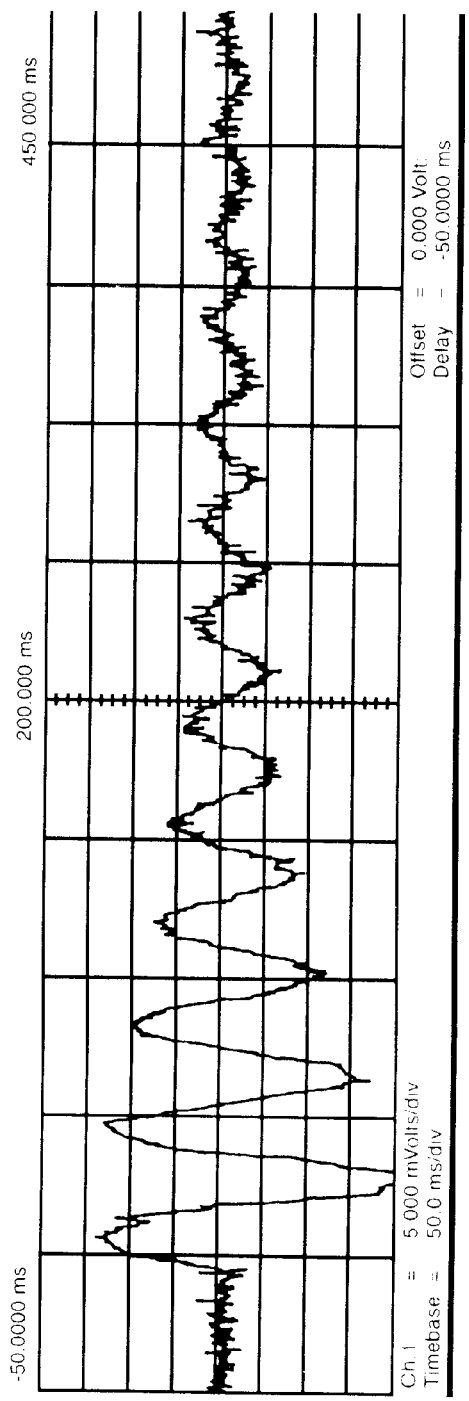
FIG. 8 is a graph of the dynamic sensing response of output voltage of strips of ion exchange polymer platinum composite (IPPC) subject to a dynamic impact loading as a cantilever.
Figure 9:
FIG. 9 is an assembly of microstrips of IPPC cut via a laser-microscope workstation for microsensing and micro-actuation.

In testing, when strips of ion exchange polymer platinum composites (IPPC) were dynamically disturbed via a dynamic impact or shock loading, nicely damped electrical response was observed as shown in FIG. 8. The dynamic response was observed to be highly repeatable with a high bandwidth to 100's of Hz. This particular property of the IPPC's of the invention is useful in a large number of applications in large motion sensing for a variety of industrial applications. As observed in FIG. 8, a strip of 4 cm in length, 0.5 cm width, and 0.2 mm thickness was subjected to a transient impact of about 10 grams per millisecond, resulting in a displacement of 13 mm at the tip in a cantilever configuration. The electrical signal generated was nicely damped with a maximum of about −20 millivolts. Since these muscles can be cut as small as desired, they present tremendous potential to micro-electro-mechanical systems (MEMS) sensing and actuation applications. FIG. 9 displays a micron-sized array of IPPC muscles cut with a laser microscope workstation.

Figure 10:
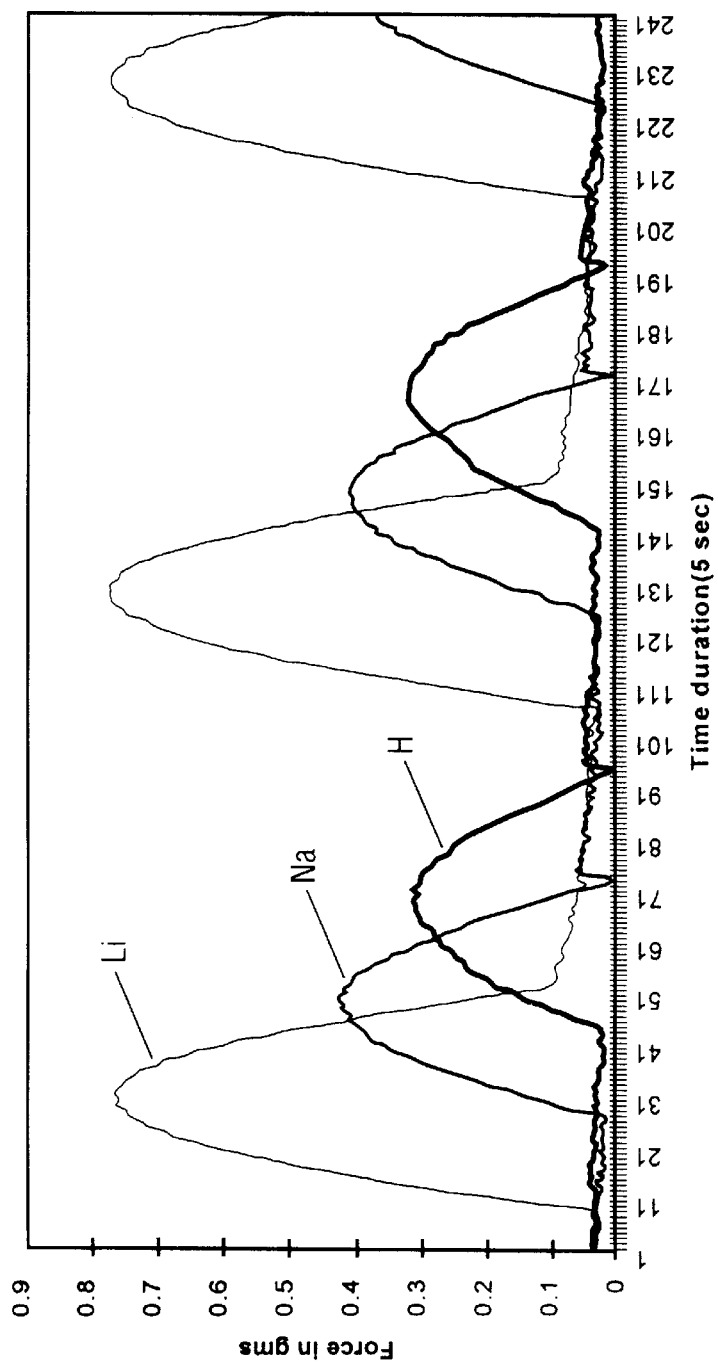
FIG. 10 is a graph comparing muscle forces (in grams) using a transducer probe for Na, H, and Li based alkali metal solutions used in IPPC fabrication.
Figure 11:
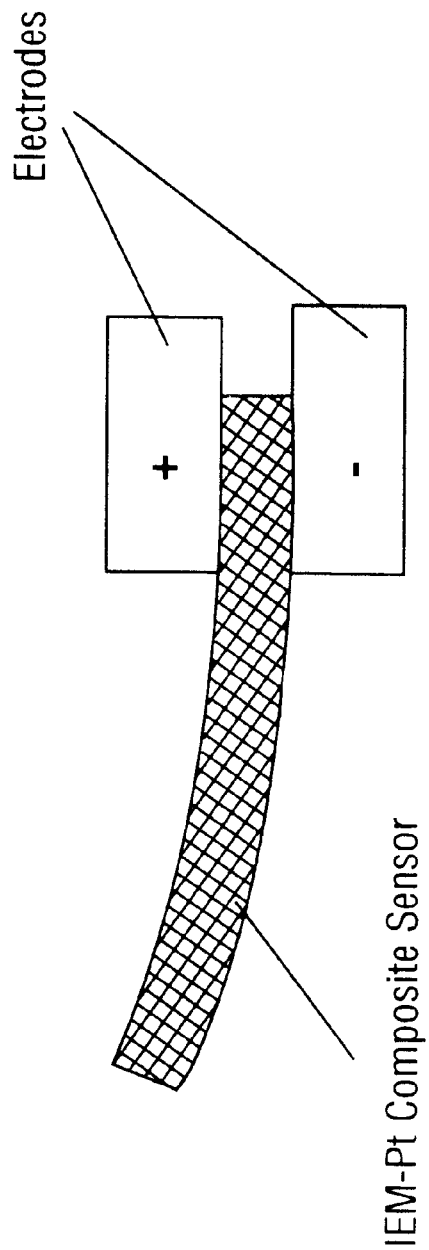
FIG. 11 is a schematic of a simple composite membrane-based sensor placed between two electrodes.

The graph of FIG. 10 shows the muscle force output based on different alkali metal solutions being used in the IPPC fabrication process. The best response occurs with use of Li. LiOH may be used rather than NaOH, and $LiBH_4$ rather than $NaBH_4$. Other alkali metal solutions may give even better results.

The muscles of the invention work best in an aqueous environment. For dry environments, the muscle can be encapsulated in latex or another impermeable yet flexible coating. The amount of water required by the membrane can be reduced when the metal layer is thicker, i.e., less porous. This appears to trap water within the membrane, and so a latex or other coating may not be required in dry environments. The muscles can also be coated with a fabric, which is useful in certain applications.

EXAMPLE 22

Displacement Sensor Devices

NAFION®-117 polymeric ion-exchange membrane was acquired from a commercially available source. The membrane was about 0.17 mm thick. The membrane was then chemically cleaned and treated with platinum to form a composite that is active under electric field of low voltage. The thickness after chemical plating was about 0.2 mm. The membrane was then fully hydrated in pure water bath. It was then cut in standard size of 30 mm×5 mm with a mass of 0.10 grams. A digital micrometer (Mitutoyo, Digimatic) was used to incrementally bend the tip of the free end of the sensor in desired direction at 1 mm interval. The other end was placed between two platinum plates (Aldrich Chemical) of 0.1 mm thickness using a plastic forceps fixed to a stand. The effective length of the sensor was measured to be 25 mm. The induced output voltage was sent to an amplifier (Crown, model 150A) before it was sent to an analog input, data acquisition card (LabView model AT-MIO-16XE-50) installed in a PC platform data acquisition system. The amplifier gain was set at its maximum, 17.3, to achieve maximum sensitivity. Before each measurement the sample was completely wetted with pure water and initially the electrodes were discharged to prevent any charge buildup due to capacitive effects.

Figure 13:
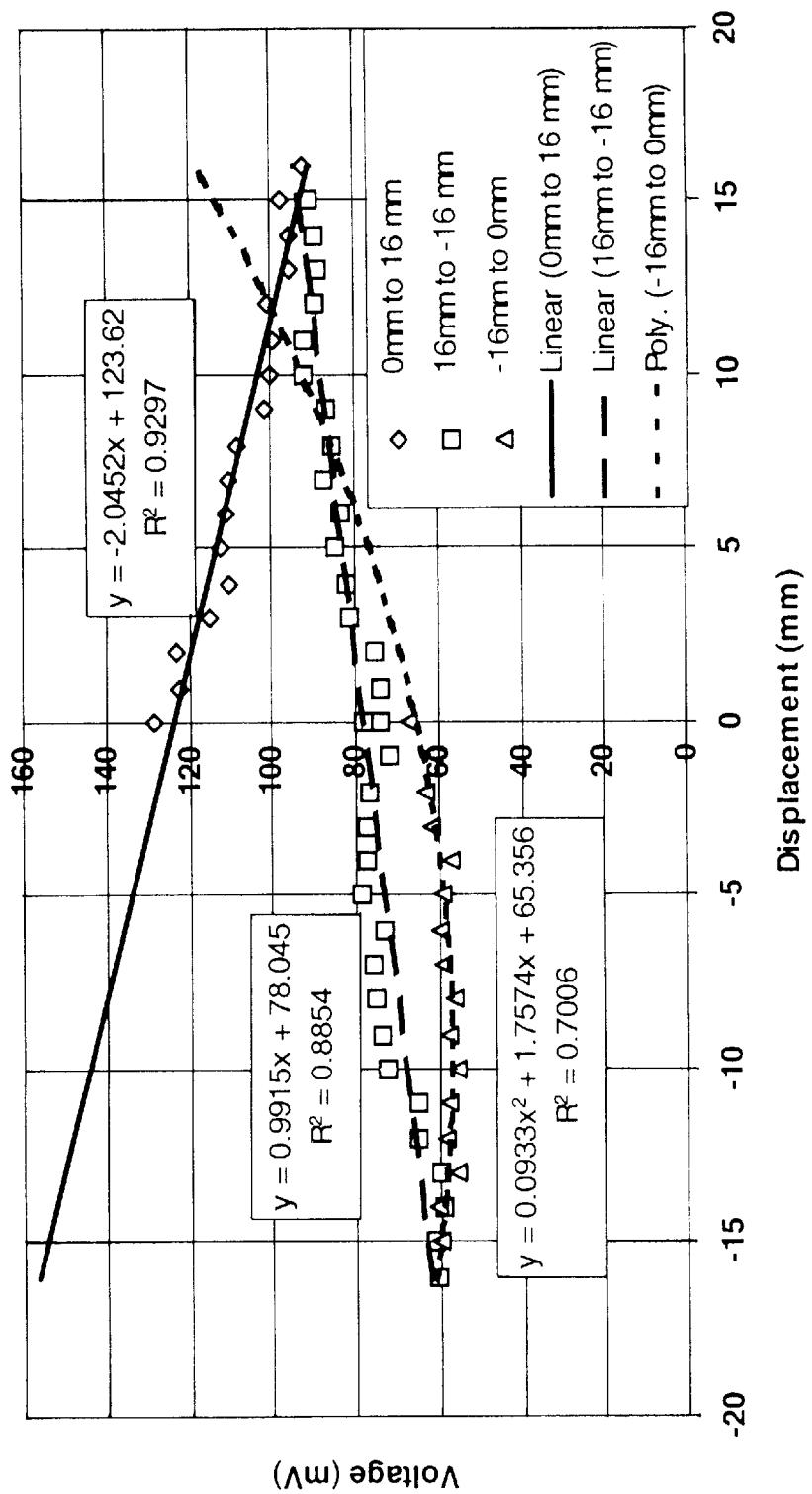
FIG. 13 is a graph of a sensor response in units of voltage (mV) for a positive displacement of the sensor tip in units of length (mm).
Figure 14:
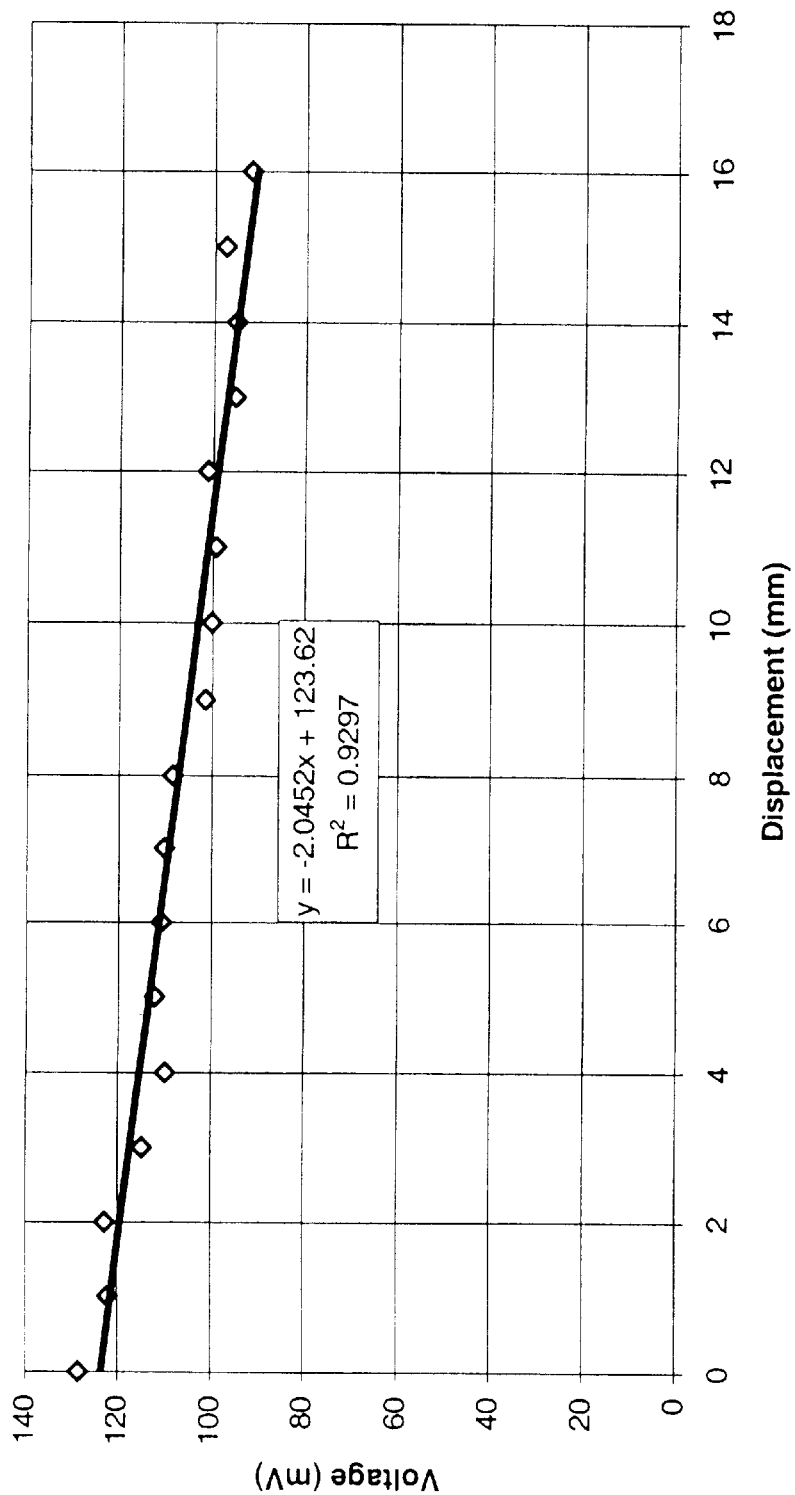
FIG. 14 is a graph of a sensor response in units of voltage (mV) for a negative displacement of the sensor tip in units of length (mm).

Experimental results showed a linear relationship between the voltage output and imposed displacement of the tip of the IEMPC sensor, see FIG. 13. When the sensor was rotated 180° to reverse polarity, displacement resulted in a linear relationship with respect to voltage output; however, the slope was reversed, see FIG. 14.

Figure 15:
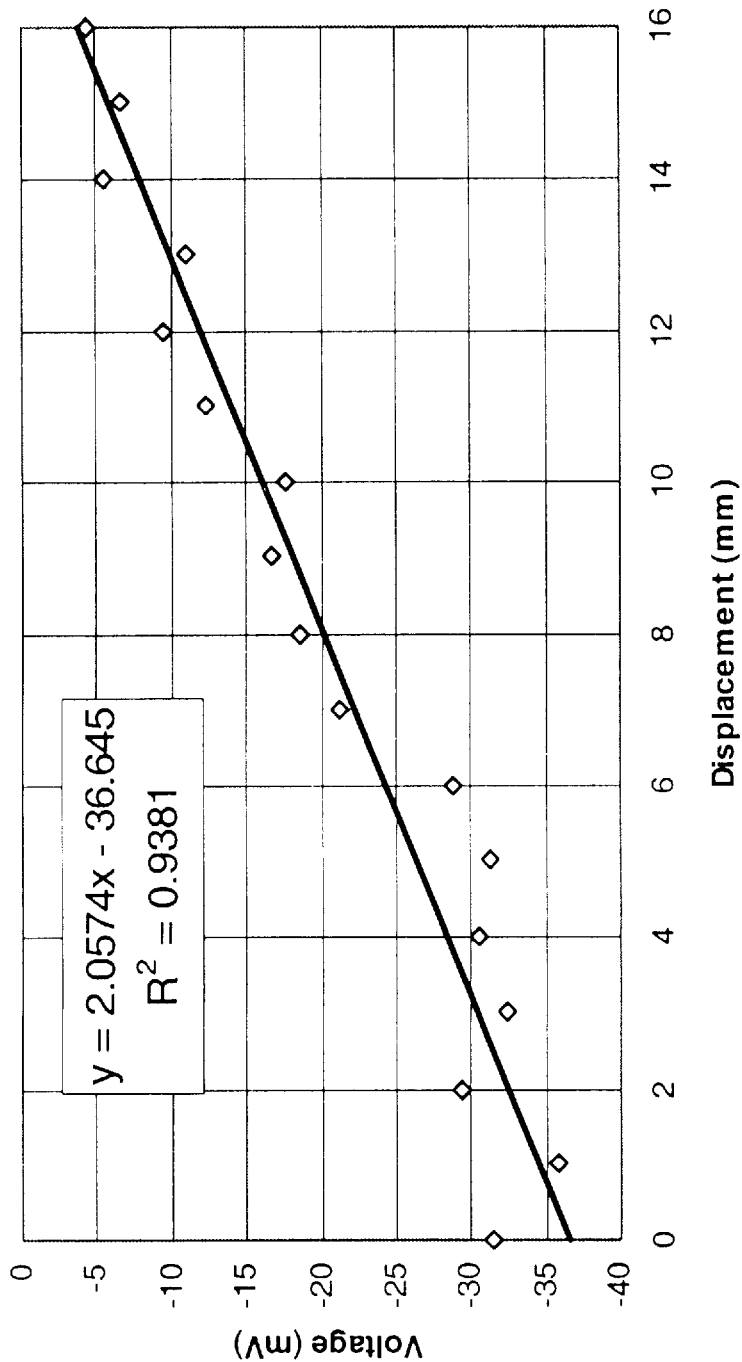
FIG. 15 is a graph showing a hysteresis curve for a sensor response in units of voltage (mV) for both positive and negative displacement of the sensor tip in units of length (mm).

When tested for displacement in negative direction, starting at neutral or horizontal level and proceeding to −16 mm displacement. However, the result followed a clearly linear trend when a complete bending cycle was initiated. This was observed during evaluation of a hysteresis curve for the film sensor, see FIG. 15. As observed in this curve, the sensor shows a linear behavior in the first, second, and third quarter of bending cycle and finally follows a parabolic trend as the fourth quarter is completed. Each quarter of the bending cycle forms a 16 mm displacement as shown in the figures.

In this example, linear behavior of the membrane was observed specifically in the positive direction of travel for each complete bending cycle. The low amplification factor of 17.3 with no signal conditioning proved sufficient. The hysteresis curve showed a linear, followed by another linear and lastly a parabolic trend as the sensor was bent in a complete cycle. Higher order polynomial approximation seemed better describing the response of the sensor in negative displacement. It was also observed that the sensor was face sensitive due in part to the capacitive nature of the sensor. Finally the use of ionic polymeric metal composites such as IEMPC as sensor may be useful where simplicity and low cost are sought.

EXAMPLE 23

Blood Pressure, Pulse Rate and Rhythm Measurement Devices

Ionic polymer-metal composites (IPMCs) are usable as biomimetic sensors. Bending an IPMC strip, either quasi-statically or dynamically, induces a voltage across its thickness. Thus they are large motion sensors. The output voltage is calibrated for a standard sensor and correlated to applied loads and stresses. IPMC sensors are manufactured and cut in any convenient size and shape suitable for BP, pulse rate, and rhythm measurement. Unlike strain gauges, where the output voltage needs to be conditioned and amplified by a factor of $10^3$ or more, IPMCs sensors produce up to hundreds of millivolt output and sense large deformations in the presence of small amplifier gains. This means they are two orders of magnitude more sensitive than conventional sensors. In addition, they don't face the shortcoming and other limitations associated with bonding of typical strain gages to the work piece.

Figure 16:
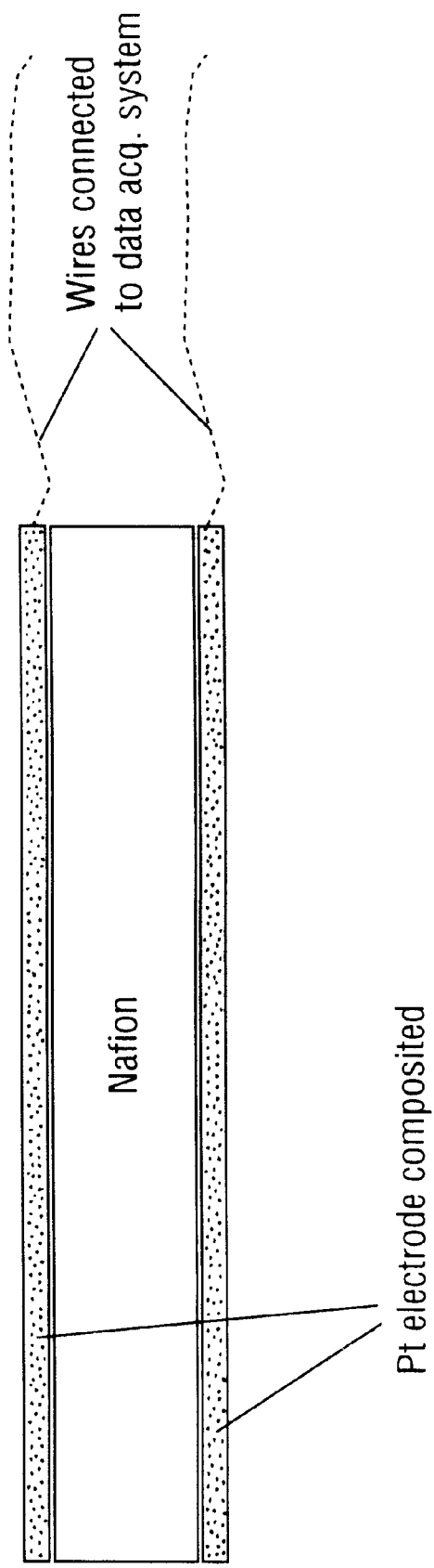
FIG. 16 is a schematic of a sensor comprising a NAFION membrane and platinum electrode surfaces.
Figure 17:
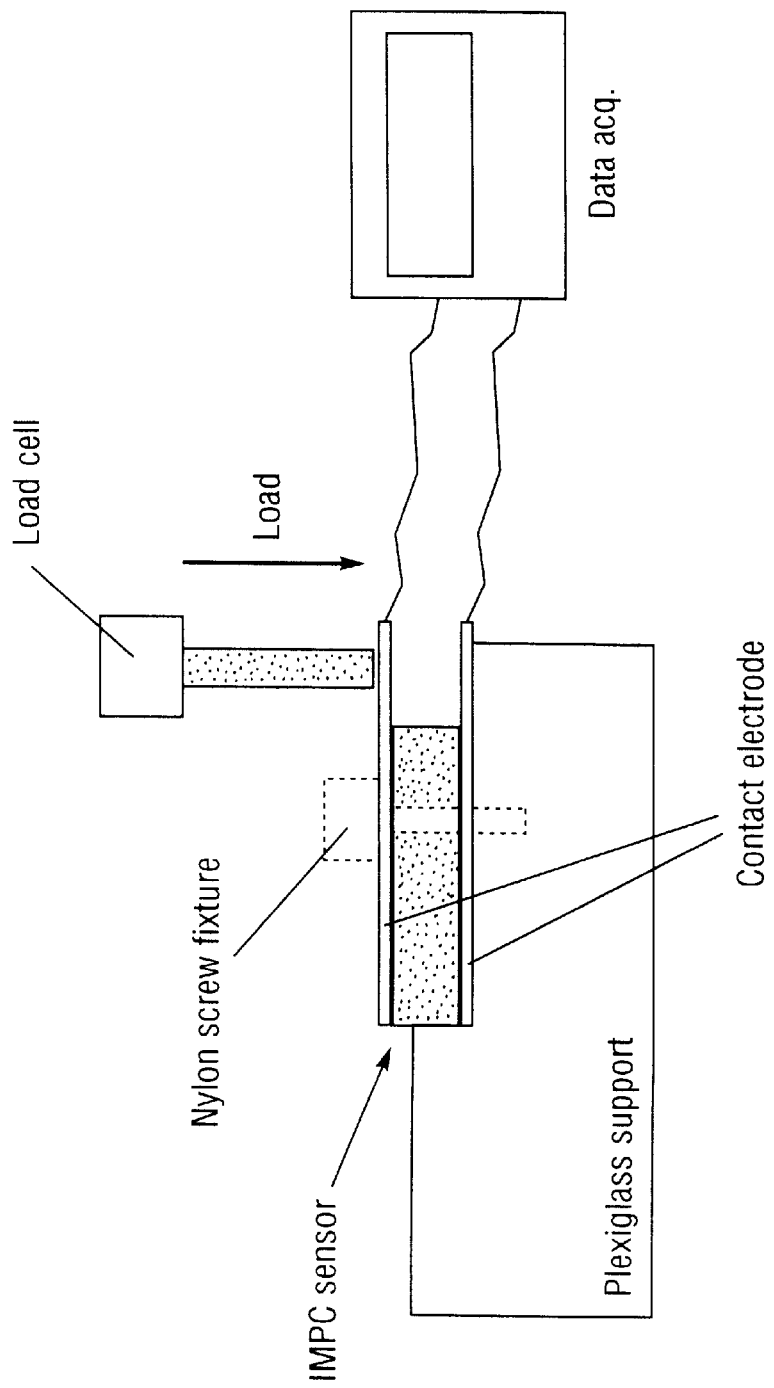
FIG. 17 is a schematic of an experimental apparatus showing a load applied to a membrane-based sensor.

FIG. 16 shows a schematic of a typical IPMC sensor. It is composed of a cationic polymer membrane and two platinum electrodes, which are composited via a chemical processing technique on both sides of the membrane. The IPMC sensors were optimized for sensing by changing multiple process parameters including time-dependent concentrations of the platinum salt and corresponding reducing agents. The typical IPMC sensor has an equivalent weight of 1,100 g/gmole $SO_3^-$ with $Li^+$. The polymer membrane used in this example is NAFION®-117 (membrane thickness of approximately 200 microns), which is the most common commercially available perfluorinated sulfonic acid ion-exchange membrane. It has TEFLON®-like backbones and side-chains terminated by the sulfonic acid group. Due to its TEFLON®-like structure, NAFION® membranes are chemically and thermally stable. NAFION® is an ionic polymer that possesses a characteristic known as "swelling" related to its water absorptivity. The extent of swelling governs the ion mobility that may affect the sensing performance of IPMCs. The polymer EW and temperature govern the extent of swelling. In this example, an isothermal condition is adopted to rule out temperature dependence of swelling.

Figure 21:
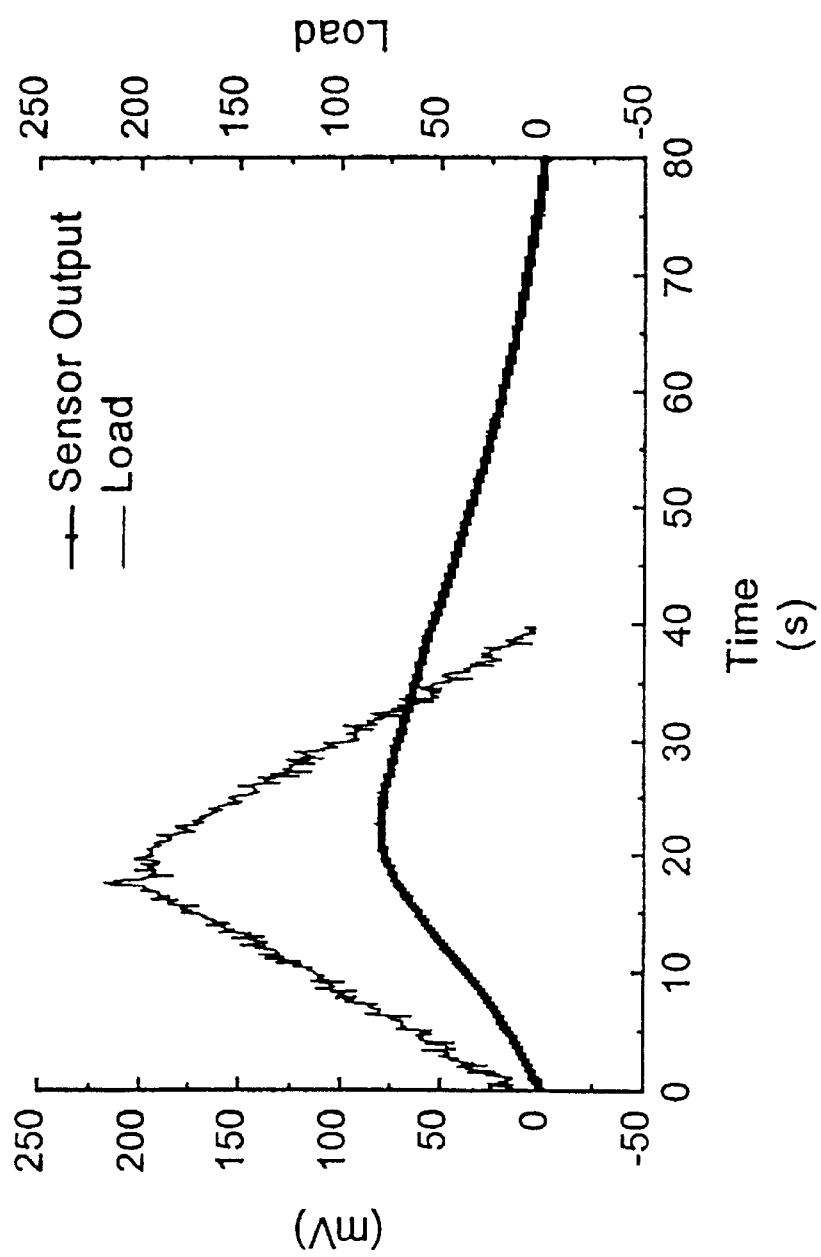
FIG. 21 is a graph showing sensor response in units of voltage (mV) for a 200 N load applied normal to the surface of the sensor.
Figure 22:
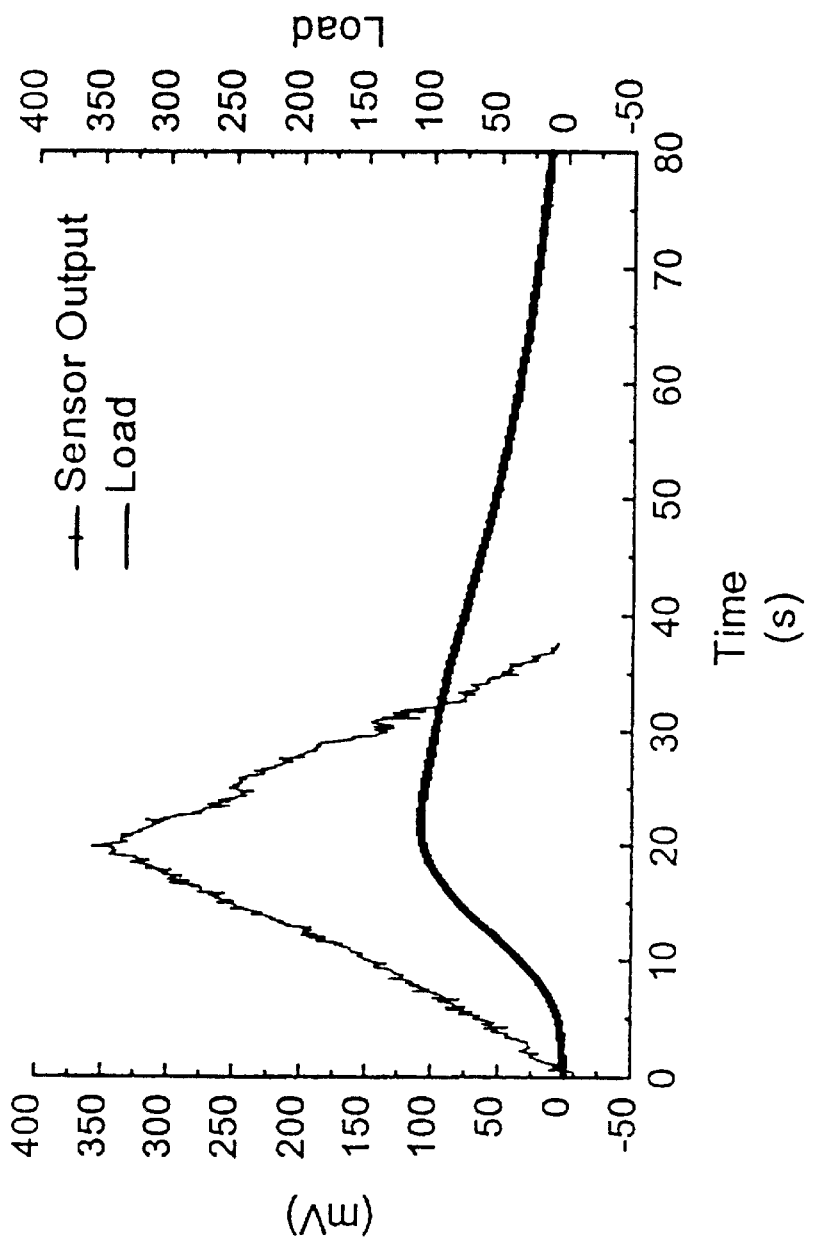
FIG. 22 is a graph showing sensor response in units of voltage (mV) for a 200 N load applied normal to the surface of the sensor.

Strips of IPMC sensors were cut to a standard size of 1×1 cm. FIG. 21 shows an illustrative schematic of the experimental setup. The IPMC sensor was sandwiched between two silver-coated contact electrodes. Initially, each contact electrode was firmly attached on both sides of the IPMC sensor by a nylon screw. Later, the nylon screw was loosed to provide a clearance of 0.5 mm from the IPMC surface. The effective surface area of the sensor was 0.25 $cm^2$ (0.5 cm×0.5 cm). The lower side of the IPMC sensor was firmly fixtured to a plexiglas platform to provide an isolated test stage. Blood pressure and rhythm were simulated by lowering the height of the load cell. The load cell (Transducer Techniques, 50 g maximum mass normal to surface) detected applied load signals that were communicated to the data acquisition system. The induced sensor output was conditioned by a signal amplifier/conditioner (Model TMO-1 AMP/COND, Transducer Techniques) and sent to an analog input data acquisition board (AT-MIO-16E-2, National Instruments). An IBM-PC based data acquisition program (LabView4.1) monitored and stored both applied loads and sensor outputs. Prior to each measurement, IMPC sensor was fully hydrated. A total of 21 data sets were acquired; these are plotted in FIG. 22 showing maximum voltage as a function of maximum load applied. The load range varied from approximately 5 g to 55 g applied mass to simulate typical blood pressures.

Figure 18:
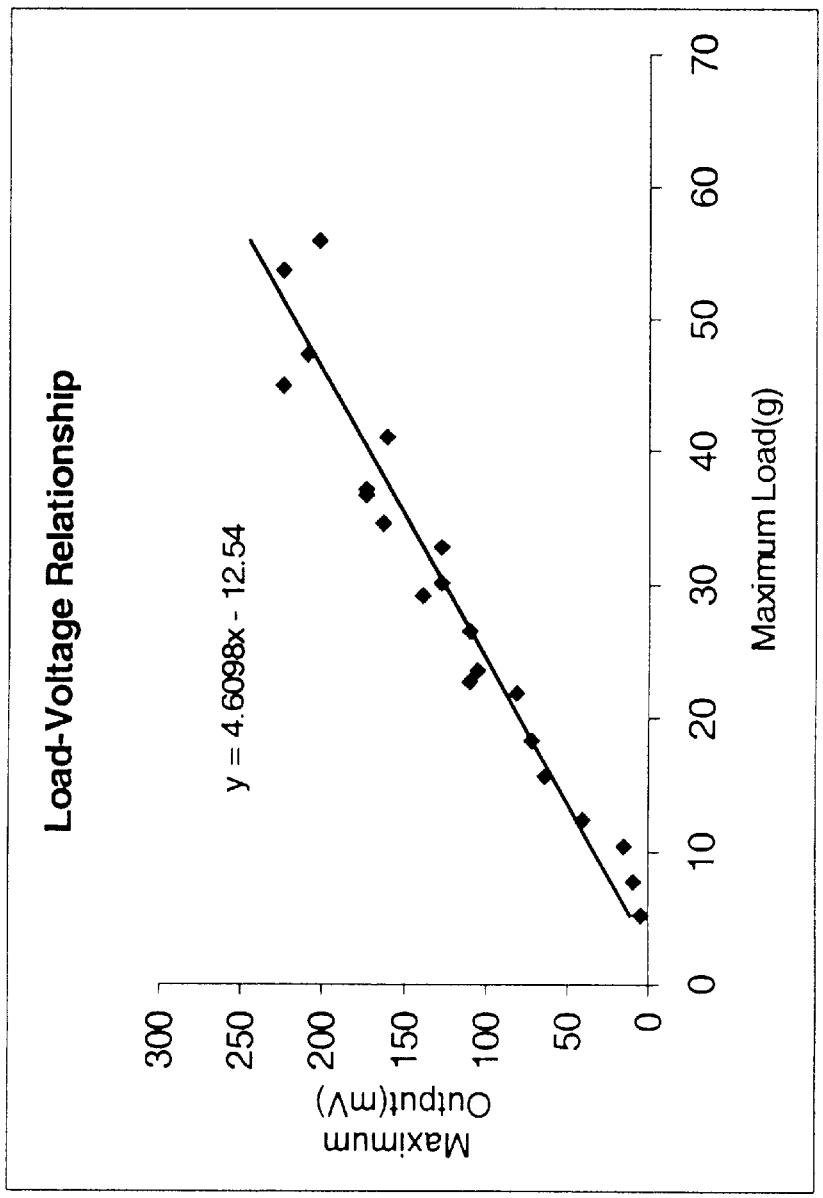
FIG. 18 is a graph of sensor output in units of voltage (mV) versus applied load in units of grams mass applied as a normal force.

In this example, a predetermined load in the range from 5 to 55 grams was applied to the sensor surface area of approximately 0.5 cm×0.5 cm. The applied load was translated into an equivalent gauge pressure of 15 mmHg to 165 mmHg. Note that the BP range of interest is 80 mmHg to 120 mmHg. The maximum sensor output voltage was in the range of approximately 5 mV to 240 mV. The results are given in FIG. 18 where the relationship of voltage output versus load displays linear behavior up to 45 g. Results also show a slight asymptotic behavior as the load increased thereafter. Between the values of approximately 20 g to 40 g, sensor output was essentially linear thus demonstrating that IPMC sensors produce consistent and reliable BP readings.

Figure 19:
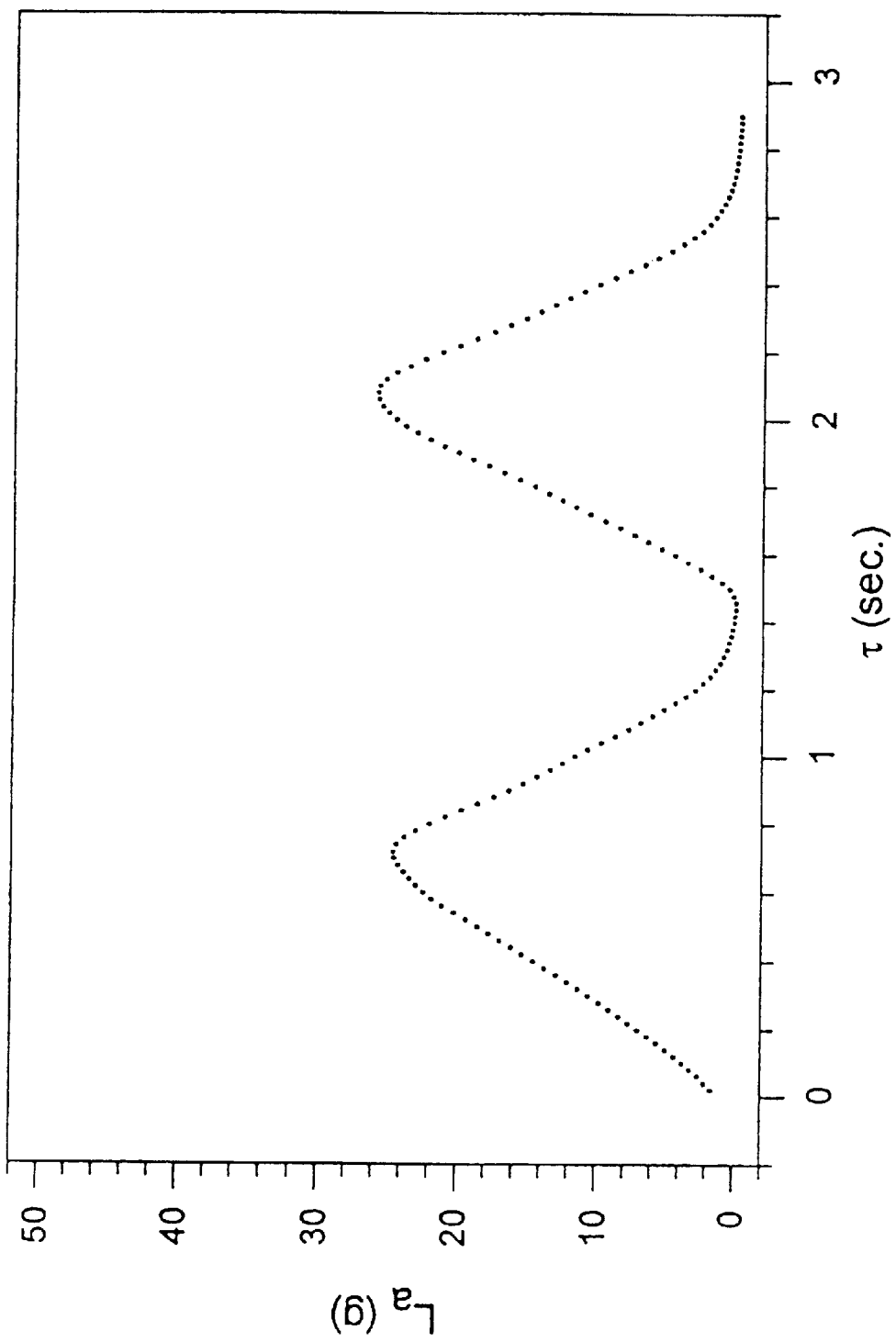
FIG. 19 is a graph of applied load in units of grams mass applied as a normal force versus time response in units of seconds.
Figure 20:
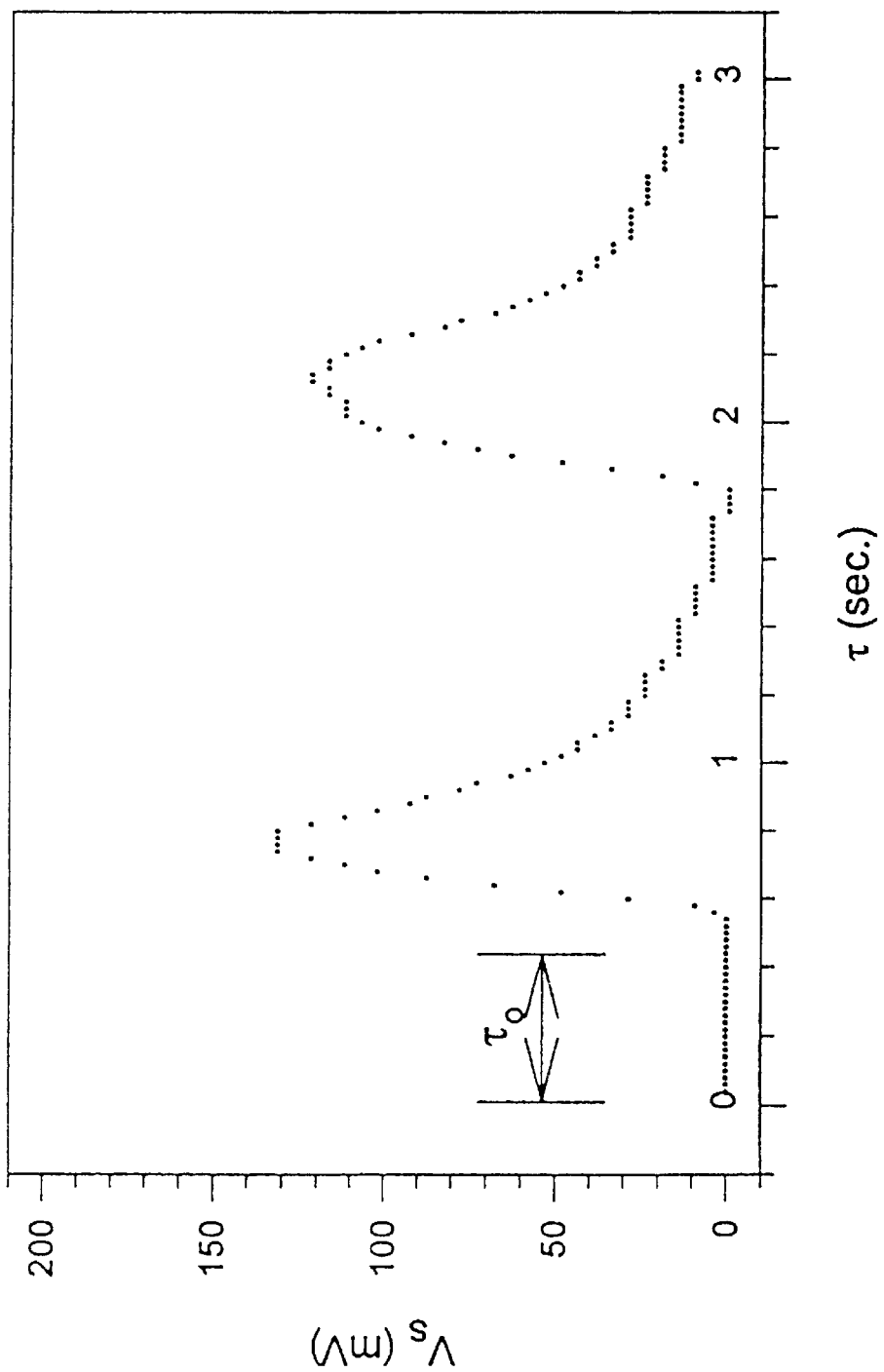
FIG. 20 is a graph of sensor response in units of voltage (mV) versus time response in units of seconds.

In FIGS. 19 and 20 a typical data set is shown for a maximum load of approximately 25 g. FIG. 19 shows applied force, $L_a$, in gram force versus time, T, in seconds. Applied forces were similar to those expected in BP measurements. The smooth temporal shape, however, does not display the sharp ascending behavior and slow descending behavior of a BP waveform, although the maximum load was appropriate for BP. FIG. 20 shows the corresponding induced voltage response of the sensor. The sensor output also showed sharp ascending behavior and slow descending behavior. The output voltage shown in FIG. 20 clearly shows a reasonable temporal response to an applied load. This examples shows that the device is effectively utilized as a BP, pulse rate, and/or rhythm sensor.

EXAMPLE 24

Pressure Transducer for Joints

In this example, a materials testing system (MTS) was used to apply consistent pure compressive loads of 200 N and 350 N across the surface of an IPMC 2 cm×2 cm strip. The output pressure response for the 200N load (73 psi) was 80 mV in amplitude and for the 350N (127 psi) it was 108 mV.

NAFION®-117 polymeric ion-exchange membrane was acquired from a commercially available source. The membrane thickness was approximately 0.17 mm. The membrane was then cleaned and deposited with platinum to form an active sensor. The thickness increased after chemical plating to approximately 0.22 mm. The membrane was then fully hydrated with deionized water. Fabricated IPMC sensors were then cut into a 2 cm×2 cm section with a 1 cm×2 cm tab for electrode attachments. The standard weight of the membranes was 0.27 grams. Prior to testing, each sensor sample was completely hydrated.

Each IPMC sensor was fixed to a plexiglas platform to provide an isolated testing stage. A uniaxial Materials Testing System (MTS) (MTS Systems Corp., Eden Prairie, Minn.) was used to apply a pure compressive load to each membrane. The plexiglas platform was placed between two precisely milled compression platens that were anchored to the MTS machine. The membranes were compressed to either 200 N or 350 N with a load and unload rate of 10 seconds. Representative load and IPMC sensor output are shown in FIG. 21 and FIG. 22. The induced output voltage was acquired by a digital oscilloscope (LeCroy, model 9304A).

In FIG. 21 and FIG. 22, results are provided for two different maximum loads; 200 N and 350 N, respectively. The sensor response and applied load are superimposed in FIG. 21 and FIG. 22. The compressive loads of 200 N and 350 N were chosen as appropriate loads that simulated the normal physiological loading of the intervertebral discs of the spine.

For the 200 N load, as shown in FIG. 21, a nonlinear relationship existed between the voltage output of the IPMC sensor and the applied load on the membrane face. In FIG. 21 and FIG. 22, data are expressed as sensor output (mV) versus applied load (N). A mean maximum output voltage for the sensor of 80 mV for 200 N of compression was observed. The sensor also exhibited a voltage relaxation phenomenon.

For the 350 N load, results are shown in FIG. 22. The voltage output of the IPMC sensor and the applied load on the membrane face are given. A mean maximum output voltage for the sensor of 108 mV for 350 N of compression was observed. At 350 N, it was clearly seen that a non-linear relationship between the voltage output of the IPMC sensor and the applied load on the membrane face existed. A slow voltage relaxation time was observed at both compressive loads, 200 N and 350 N. The viscoelastic nature of the NAFION® membrane is one of potentially many factors responsible for such a non-linearity that leads to such behavior.

This example demonstrates that voltage response of the IPMC sensor correlates well with applied compressive loading. In general, the voltage response (sensor output) increases as the load increases. The prospect of the IPMC sensors for future use as pressure sensing devices is apparent. The sensors of the present invention are customizable to relatively small size thereby allowing sensor placement in regions of the spine where a standard commercial micropressure transducer cannot be placed. The flexible nature of the IPMC reduces the risk of damage to both the sensor and the tissue into which it is inserted. There is no risk of a damaged sensor with fluid exposure, unlike that of the existing pressure transducers. The sensors of the present invention are not limited in function if exposed to fluid. Furthermore, the sensors of the present invention do not require meticulous sealing with epoxy that may increase the bulk and adversely affect their use.

Although the invention has been described in detail with particular reference to these preferred embodiments, other embodiments can achieve the same results. Variations and modifications of the present invention will be obvious to those skilled in the art, and it is intended to cover in the appended claims all such modifications and equivalents. The entire disclosures of all references, applications, patents, and publications cited above, are hereby incorporated by reference.

What is claimed is:

1. A sensing element comprising:
   an ion exchange polymer;
   a porous conductive layer embedded in said polymer with penetration inside said polymer comprising at least two embedded electrodes wherein movement of said polymer in a dry environment generates an electrical potential between at least two of said at least two electrodes; and
   an impermeable flexible coating encapsulating said ion exchange polymer.

2. The element according to claim 1, wherein said generated electrical potential feeds back to said sensing element.

3. The element according to claim 1, wherein said generated electrical potential feeds back to said sensing element to control a position of said sensing element.

4. The element according to claim 1 wherein said at least two embedded electrodes comprise dendritically embedded electrodes.

5. The element according to claim 1, wherein said flexible coating provides biocompatibility with biological material in which said sensing element is placed.

6. The element according to claim 1, wherein said flexible coating permits transport of at least one member selected from the group consisting of mass transport and energy transport.

7. The element according to claim 1, wherein said flexible coating comprises a non-porous material.

8. An actuating device comprising:
   an ion exchange polymer;
   a porous conductive layer embedded in said polymer with penetration inside said polymer comprising at least two embedded electrodes wherein application of an electrical potential across said electrodes causes movement of said polymer in a dry environment; and an impermeable flexible coating encapsulating said ion exchange polymer.

9. The actuating device according to claim 8, further comprising embedded feedback electrodes for sensing motion.

10. The element according to claim 8 wherein said at least two embedded electrodes comprise dendritically embedded electrodes.

11. A sensing element comprising:

an ion exchange polymer;

a porous conductive layer embedded in said polymer with penetration inside said polymer comprising at least two embedded electrodes wherein deformation of said polymer generates an electrical potential between at least two of said at least two electrodes; and an impermeable flexible surrounding coating attached to and forming an outer surface of said polymer and a portion of the electrodes and which moves in conformity with the deformation of said polymer in a dry environment.

12. The element according to claim 11, wherein said flexible surrounding coating encapsulates said sensing element.

13. The element according to claim 11, wherein said flexible surrounding coating provides biocompatibility with biological material in which said sensing element is placed.

14. The element according to claim 11, wherein said flexible surrounding coating permits transport of at least one member selected from the group consisting of mass transport and energy transport.

15. The element according to claim 11 wherein said at least two embedded electrodes comprise dendritically embedded electrodes.

16. A sensing element comprising:

an ion exchange polymer;

a porous conductive layer comprising a sufficient thickness to trap water within said ion exchange polymer embedded in said polymer with penetration inside said polymer comprising at least two embedded electrodes wherein movement of said polymer in a dry environment generates an electrical potential between at least two of said at least two electrodes.

17. The element according to claim 16, wherein said generated electrical potential feeds back to said sensing element.

18. The element according to claim 16, wherein said generated electrical potential feeds back to said sensing element to control a position of said sensing element.

19. An actuating device comprising:

an ion exchange polymer;

a porous conductive layer comprising a sufficient thickness to trap water within said ion exchange polymer embedded in said polymer with penetration inside said polymer comprising at least two embedded electrodes wherein application of an electrical potential across said electrodes causes movement of said polymer in a dry environment.

20. The actuating device according to claim 19, further comprising embedded feedback electrodes for sensing motion.

\* \* \* \* \*